US007393658B2

(12) United States Patent
Carbonell et al.

(10) Patent No.: US 7,393,658 B2
(45) Date of Patent: Jul. 1, 2008

(54) PRION PROTEIN BINDING MATERIALS AND METHODS OF USE

(75) Inventors: Ruben G. Carbonell, Raleigh, NC (US); Honglue Shen, Raleigh, NC (US); Patrick V. Gurgel, Raleigh, NC (US); Viteros Wiltshire-Lyerly, Raleigh, NC (US); David J. Hammond, Laytonsville, MD (US); Steven J. Burton, Little Eversden (GB)

(73) Assignees: Pathogen Removal and Diagnostic Technologies, Inc., Wilmington, DE (US); North Carolina State University, Raleigh, NC (US)

( * ) Notice: Subject to any disclaimer, the term of this patent is extended or adjusted under 35 U.S.C. 154(b) by 6 days.

(21) Appl. No.: 10/817,117

(22) Filed: Apr. 2, 2004

(65) Prior Publication Data

US 2005/0014196 A1 Jan. 20, 2005

Related U.S. Application Data

(60) Provisional application No. 60/460,474, filed on Apr. 4, 2003.

(51) Int. Cl.
*G01N 33/53* (2006.01)
(52) U.S. Cl. ..................................... 435/7.8; 424/204.1
(58) Field of Classification Search ........................ None
See application file for complete search history.

(56) References Cited

U.S. PATENT DOCUMENTS

| | | | |
|---|---|---|---|
| 5,010,175 A | 4/1991 | Rutter et al. | |
| 5,133,866 A | 7/1992 | Kauvar | |
| 5,281,539 A | 1/1994 | Schramm | |
| 5,312,730 A | 5/1994 | Piran et al. | |
| 5,498,538 A | 3/1996 | Kay et al. | |
| 5,750,361 A | 5/1998 | Prusiner et al. | |
| 5,808,011 A | 9/1998 | Gawryl et al. | |
| 5,834,318 A | 11/1998 | Buettner et al. | |
| 5,888,834 A | 3/1999 | Ishikawa et al. | |
| 6,221,614 B1* | 4/2001 | Prusiner et al. | 435/7.1 |
| 6,379,905 B1 | 4/2002 | Fishleigh et al. | |
| 6,437,102 B1 | 8/2002 | Lee et al. | |
| 6,451,541 B1 | 9/2002 | Winnacker et al. | |
| 6,750,025 B1* | 6/2004 | Hammond et al. | 435/7.1 |
| 2003/0092094 A1 | 5/2003 | Vey et al. | |

FOREIGN PATENT DOCUMENTS

| | | |
|---|---|---|
| WO | WO 92/00091 | 1/1992 |
| WO | WO 01/77687 | 10/2001 |
| WO | WO 03/016904 | 2/2003 |

OTHER PUBLICATIONS

Foster et a., Studies on the removal of abnormal prion protein by Processes used in the manufacture of human plasma products. (2000) Vox sanginis. vol. 78, p. 86-95.*
Kragten et al., Glyceraldehyde-3-phosphate Dehydrohenase, the Putative Target of Antiapoptotic Compounds CGP 3466 and R-(-)-Deprenyl. (1998) Journal of Biological Chemistry vol. 273, No. 10. p. 5821-5828.*
Tosoh Bioscience LLc, Data Sheet and Manual, www.tosohbioscience.com.*
Aubry et al., "N-Methyl Peptides. IV. Water and Beta-Turn in Peptides. Crystal Structure of N-Pivaloyl-L-Prolyl-N, N'-Dimethyl-D-Alaninamide in the Anhydrous and Monohydrated States", *Int. J. Pept. Protein Res.*, 18: 195-202 (1981).
Caughey, B., et al., "Binding of the Protease-Sensitive Form of Prion Protein PrP to Sulfated Glycosaminoglycan and Congo Red", *Journal of Virology*, 68: 2135-2141 (1994).
Degrado, W.F., "Design of Peptides and Proteins", *Adv. Protein Chem*:.39, 51-124, (1988).
Devlin, J.J. et al., "Random Peptide Libraries: A Source of Specific Protein Binding Molecules", *Science*: 249, 404-406 (1990).
Fischer, M.B. et al., "Binding of Disease-Associated Prion Protein to Plasminogen",*Nature*: 408, 479-483 (2000).
Furka, A. et al. "General Method for Rapid Synthesis of Multicomponent Peptide Mixtures", *Int. J. Peptide Protein Res.*:37, 487-493 (1991).
Ingrosso, L., et al., "Congo Red Prolongs the Incubation Period in Scrapie-Infected Hamsters", *Journal of Virology*: 69, 506-508 (1995).
Jameson, B.A. et al., "A Rationally Designed CD4 Analogue Inhibits Experimental Allergic Encephalomyelitis", *Nature*: 368, 744-746 (1994).
Kascsak, R.J., et al., "Immunodiagnosis of Prion Disease", *Immunological Invest.*: 26, 259-268 (1997).
Lam, K.S. et al., "A New Type of Synthetic Peptide Library for Identifying Ligand-Binding Activity", *Nature*: 354,82-84 (1991).
Soto et al., "Reversion Of Prion Protein Conformational Changes By Synthetic β-Sheet Breaker Peptides", *Lancet*: 355, 192-197 (2000).
Merrifield, B. "Solid Phase Synthesis", *Science*: 232, 341-3479 (1986).

(Continued)

*Primary Examiner*—Bruce R. Campell
*Assistant Examiner*—Agnieszka Boesen
(74) *Attorney, Agent, or Firm*—Nixon Peabody LLP

(57) ABSTRACT

Prion protein binding materials and methods for using the binding materials to detect or remove a prion protein from a sample, such as a biological fluid or an environmental sample. The binding materials are capable of binding to one or more forms of prion protein including cellular prion protein (PrPc), infectious prion protein (PrPsc), recombinant prion protein (PrPr), and proteinase resistant prion protein (PrPres). Prions from various species, including humans and hamsters, are bound by the binding materials.

26 Claims, 4 Drawing Sheets

OTHER PUBLICATIONS

Needleman, S.B. et al. "A General method Applicable to the Search for Similarities in the Amino Acid Sequence of Two Proteins", *J. Mol. Biol.*: 48, 443-453 (1970).

Pearson, W.R. et al. "Impoved Tools for Biological Sequence Comparison", *Proc. Natl. Acad. Sci. U.S.A.*:85, 2444-2448 (1988).

Priola, S.A., et al., "Porphyrin and Phthalocyanine Antiscrapie Compounds", *Science*: 287, 1503-1506 (2000).

Prusiner, S.B., "Molecular Biology of Prion Diseases", *Science*: 252, 1515-1522 (1991).

Rose et al. "Turns In Peptides And Proteins", *Molecular Biology of Prion Diseases Adv. Protein Chem.*: 37, 1-109 (1985).

Safar, J. et al., "Eight Prion Strains Have PrP(Sc) Molecules With Different Conformations", *Nature Medicine*: 4, 1157-1165 (1998).

Samson, W.K. et al. "A 35 Amino Acid Fragment of Leptin Inhibits Feeding in the Rat", *Endocrinology*: 137, 5182-5185 (1996).

Soto, C. et al., "Reversion of Prion Protein Conformational Changes in Synthetic Beta-Sheet Breaker Peptides", *Lancet*: 355, 192-197 (2000).

Stockell, et al., "Prion Protein Selectively Bindes Copper(II) Ions", *Biochemistry*: 37, 7185-7193 (1998).

Tagliavani, F., et al., "Effectiveness of Anthracycline Against Experimental Prion Diseases in Syrian Hamsters," *Science*: 276, 1119-1122 (1997).

Caspi et al., "The Anti-Prion Activity Of Congo Red", J. Biol. Chem.: 273, 3484-3489 (1999).

McHattle et al., "Clusterin Prevents Aggregation Of Neuropeptide 106-126 In Vitro", *Biochem. Biophys. Res. Commun*: 259, 336-340 (1999).

* cited by examiner

A 1 2 3 4 5 6 7 8 9 10 11 12 13

B 1 2 3 4 5 6 7 8 9 10 11 12 13 14

C 1 2 3 4 5 6 7 8 9 10 11 12 13

D 1 2 3 4 5 6 7 8 9 10 11 12 13

1  2  3  4  5  6   7  8   9 10 11 12 13 14 15 16

SEQUENCE LISTING

<160> NUMBER OF SEQ ID NOS: 1

<210> SEQ ID NO 1
<211> LENGTH: 8
<212> TYPE: PRT
<213> ORGANISM: Artificial Sequence
<220> FEATURE:
<223> OTHER INFORMATION: Synthetic

<400> SEQUENCE: 1

Pro His Gly Gly Gly Trp Gly Gln
1               5

PRION PROTEIN BINDING MATERIALS AND METHODS OF USE

CROSS-REFERENCE TO RELATED APPLICATIONS

This application claims benefit of U.S. Provisional Patent Application Ser. No. 60/460,474 filed Apr. 4, 2003.

FIELD OF THE INVENTION

This invention relates to the field of protein binding and more particularly relates to materials that bind to prion proteins and methods of using the prion protein binding materials to detect or remove prions from biological samples.

BACKGROUND OF THE INVENTION

Native or cellular prion protein "PrPc" is widely distributed throughout the mammalia and has a particularly well-conserved amino acid sequence and protein structure. Infectious prions are thought to be composed of a modified form of the normal cellular (PrPc) prion protein and are called "PrPsc". Prions have some properties in common with other infectious pathogens, but do not appear to contain nucleic acid. Instead, it is proposed that a post-translational conformational change is involved in the conversion of non-infectious PrPc into infectious PrPsc during which α-helices are transformed into β-sheets. PrPc contains three α-helices and has little β-sheet structure; in contrast, PrPsc is rich in β-sheet. The conversion of PrPc to PrPsc is believed to lead to the development of transmissible spongiform encephalopathies (TSEs) during which PrPsc accumulates in the central nervous system and is accompanied by neuropathologic changes and neurological dysfunction. PrPsc, often referred to as the "scrapie" form of the prion protein, is considered necessary, and possibly sufficient, for the transmission and pathogenesis of these transmissible neurodegenerative diseases of animals and humans.

Specific examples of TSEs include scrapie, which affects sheep and goats; bovine spongiform encephalopathy (BSE); transmissible mink encephalopathy, feline spongiform encephalopathy and chronic wasting disease (CWD). In humans, TSE diseases may present themselves as kuru, Creutzfeldt-Jakob disease (CJD), Gerstmann-Straüssler-Scheinker Syndrome (GSS), fatal insomnia and variant Creutzfeldt-Jakob disease (vCJD). vCJD recently emerged in humans as a result of the BSE epidemic in Britain and is most probably caused by the consumption of food products derived from cattle infected with BSE or "mad cow disease". An unknown number of people in the UK ingested food potentially contaminated with nervous tissue from BSE-infected cattle during the mid 1980s to early 1990s. Because the incubation period for the orally contracted disease may be more than 20 years in humans, the true incidence of vCJD may not become apparent for many years. To date, over 150 people are known to have contracted the disease, primarily in the UK; however, cases have been reported in Canada, France, Hong Kong, Ireland, Italy, and the US. The export of contaminated bovine feed products from the UK worldwide indicates a possible global presence of BSE and hence the probability of vCJD. Consistent with these observations is the detection of BSE in most European countries, Japan, Canada, USA and Israel. Consequently, the ability to detect and remove infectious prion protein from a variety of materials including food products is of profound importance.

A characteristic of all TSEs is the lack of a measurable host immune response to the agent. Consequently, no antibodies specific for TSCs have been currently identified. Moreover, the lack of a known nucleic acid sequence precludes the use of polymerase chain reaction-based diagnostic methods. Thus, no conventional serologic test can be used to identify infected animals. Recently, improved immunological-based techniques have been used to identify PrPsc in brains from slaughtered animals.

In addition to ingestion of infected products of bovine origin, blood transfusion and organ transplantation represent another mode of transmission of vCJD among humans. The risk of transmissibility of vCJD in humans by blood transfusion is currently unknown, but, based on data from experimental animal models including transmission from sheep experimentally infected orally with BSE and sheep naturally infected with scrapie, appears to be a very likely possibility and has already most probably accounted for one human to human transmission of vCJD. Unlike other human TSEs, PrPsc is present in the lymphoreticular system of vCJD patients, thereby increasing the probability of the infectious agent being in blood and its transmission through blood transfusion. Other factors elevating concern about the risk of transmission by transfusion include the unknown, but presumably high, numbers of people exposed to BSE and lack of a pre-clinical diagnostic test for vCJD. Moreover, the virulence of vCJD appears to be enhanced following species adaptation in primates and mice suggesting that human to human transmission may be more efficient than cow to human. Thus, there is an urgent need for methods to prevent the transmission of vCJD by blood transfusion. Such measures may include early identification of infected donors and their deferral, removal and inactivation of TSE agents in animal derived food and health products intended for animal or human consumption or applications, human and bovine blood-derived products, and organ transplants. Unfortunately, TSE infectivity is remarkably resistant to chemical and physical methods of inactivation, and a selective method of inactivation is elusive.

A number of materials have been identified that bind to prion protein. Combinatorial peptide libraries have been screened for ligands that bind to the octapeptide repeat sequence (PHGGGWGQ) (SEQ ID NO:1) found in all known mammalian prion proteins and a series of ligands were discovered, as described in PCT/US01/11150. Other materials include ligands that interact with amyloid plaque e.g., Congo Red (Ingrosso, L., et al., Congo Red Prolongs the Incubation Period in Scrapie-infected Hamsters. *J. Virology* 69:506-508 (1995)); 4-iodo, 4-deoxy doxorubicin (Tagliavini, F., et al., Effectiveness of Anthracycline Against Experimental Prion Diseases in Syrian Hamsters. *Science* 276:1119-1122 (1997)); amphotericin B, porphyrins and phthalocyanines (Priola, S. A., et al., Porphyrin and Phthalocyanine Antiscrapie Compounds, *Science* 287:1503-1506 (2000)); metals (Stockel et al., *Biochemistry,* 37, 7185-7193 (1998)); peptides that interact with PrP to form complexes (see U.S. Pat. No. 5,750,361 to Prusiner et al. and Soto, C. et al., Reversion of Prion Protein Conformational Changes in Synthetic β-sheet Breaker Peptides, *Lancet,* 355:192-197 (2000)); heparin and other polysulphated polyanions (Caughey, B., et al., Binding of the Protease-sensitive Form of Prion Protein PrP to Sulphated Glycosaminoglycan and Congo Red, *J. Virology* 68:2135-2141(1994)); antibodies (Kascsak, R. J., et al., Immunodiagnosis of Prion Disease, *Immunological Invest.* 26:259-268 (1997)); and other proteins, e.g. plasminogen (Fischer, M. B. et al., Binding of Disease-associated Prion Protein to Plasminogen., *Nature* 408:479-483 (2000)). Ion exchange chromatography has been used to purify blood components, such as hemoglobin, from prion contamination (U.S. Pat. No. 5,808,011 to Gawryl et al.). However, the chromatographic material taught by Gawryl et al. binds the hemoglobin, and the purified hemoglobin is subsequently collected by gradient elution. Currently, no material has been fully characterized or found to be able to bind to prion from a wide variety of media.

To date, human TSE diseases are 100% fatal. Unfortunately, even though a number of compounds including amphotericins, sulphated polyanions, Congo Red dye and anthracycline antibiotics have been reported as prospective therapeutic agents, all have demonstrated only modest potential to impede prion propagation, and none have been shown to have any effect on the removal of pre-existing prions from an infected host in a controlled clinical study. Thus, there remains an urgent need for new therapeutic agents.

The assembly and disassembly of normally soluble proteins into conformationally altered and insoluble forms are thought to be a causative process in a variety of other diseases, many of which are neurological diseases. The relationship between the onset of the disease and the transition from the normal to the conformationally altered protein is poorly understood. Examples of such insoluble proteins in addition to prion include: β-amyloid peptide in amyloid plaques of Alzheimer's disease and cerebral amyloid angiopathy; α-synuclein deposits in Lewy bodies of Parkinson's disease, tau in neurofibrillary tangles in frontal temporal dementia and Pick's disease; superoxide dismutase in amyotrophic lateral sclerosis; and huntingtin in Huntington's Disease. Often these highly insoluble proteins form aggregates composed of non-branching fibrils with the common characteristic of a β-pleated sheet conformation.

Methodologies that can readily separate or that can distinguish between two or more different conformational forms of a protein, e.g., PrPc and PrPsc, are needed to understand the process of conversion and to find structures that will specifically interact with the disease associated form. Current methodologies for separating or distinguishing between isoforms of proteins include: differential mobility in polyacrylamide gels in the presence of a chaotrope such as urea, i.e., transverse urea gradient (TUG) gels; differential sensitivity to protease treatment, e.g., proteinase K (PK) and the detection of the PK-resistant digest product of PrPsc referred to as PrPres; differential temperature stability; relative solubility in non-ionic detergents; and the ability for fibrillar structures to bind certain chemicals, e.g., Congo Red and isoflavin S. However, there remains an unmet need to identify additional prion binding materials. There also remains a need to identify high affinity binding materials that are specific for the conformationally altered protein and especially forms associated with disease. Such reagents would be useful for developing possible diagnostic kits, separation and purification of the different forms of protein, for removal of infectious forms of the disease from therapeutic agents, biological products, vaccines and foodstuffs, and for therapy.

SUMMARY OF THE INVENTION

Materials that bind to prion proteins and methods for using the prion protein binding materials (hereinafter "binding materials") are provided. In some embodiments, the binding materials are polymer particles, preferably chromatographic resins, that bind with selectivity and specificity to prion analytes. In other embodiments, the binding materials are inorganic materials that bind with selectivity and specificity to prion analytes. The binding materials are capable of binding to one or more forms of prion protein including cellular prion protein (PrPc), infectious prion protein (PrPsc), and recombinant prion protein (PrPr). Prions from various species, including humans and hamsters, are bound by the binding materials. Compositions containing the binding materials on a support such as a chromatography column are also provided.

The binding materials are useful for detecting, binding to, isolating, removing, eliminating, extracting or separating a prion protein in or from a sample, such as a biological fluid or an environmental sample. The binding materials are used to remove all forms of prion protein from a sample or can be selectively chosen to detect or remove a single form of prion protein. The binding materials can, therefore, be used to distinguish between infectious and non-infectious prion protein in a sample from patients afflicted with human TSEs and animals afflicted with scrapie, BSE and CWD. In one embodiment, one or more prion proteins are removed from a biological fluid using the binding materials described herein and the purified or decontaminated biological fluid is then administered, or returned, to an animal or human. Hemodialysis techniques may be employed in this embodiment. The binding materials are also useful for the detection of one or more prion proteins in a sample.

Another aspect of the invention provides a method for identifying additional binding materials, particularly binding materials specific for the conformationally altered forms of proteins, some of which are involved in the development of diseases.

Other features and advantages of the invention will be apparent from the following detailed description and preferred embodiments.

DETAILED DESCRIPTION

Figure 1:
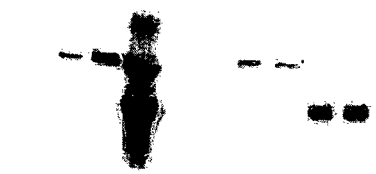
FIG. 1 is a photograph of a Western blot showing the binding of endogenous PrPc from human plasma samples to prion binding materials and appropriate controls.
Figure 1:
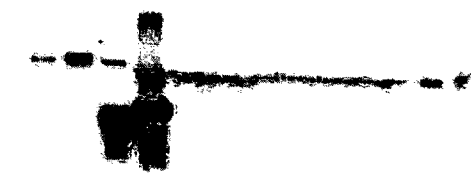
Figure 1:
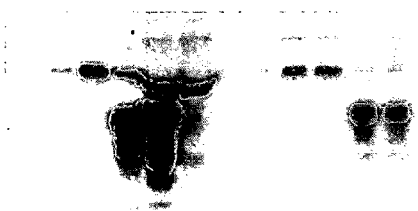
Figure 1:
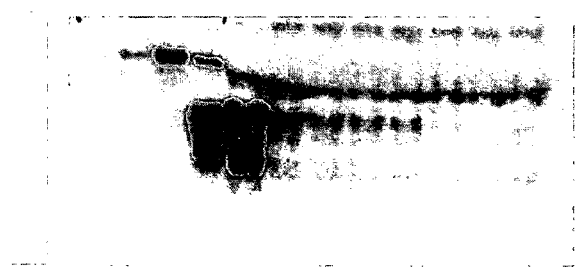

Materials that bind to prion proteins and methods for using the prion protein binding materials are described herein. The binding materials are polymeric materials, such as chromatographic resins or beads, or inorganic materials, such as aluminum oxide, that bind with specificity and affinity to prion proteins. The polymeric materials contain one or more of the following functional groups: a negatively charged moiety; a positively charged moiety; an uncharged moiety and a hydrophobic moiety. Preferably, the polymeric binding materials have a functional group bound to a methacrylate or polymethacrylate matrix backbone.

The binding materials form a complex with a prion protein in a sample and are useful in methods for detecting, binding to, isolating, removing, eliminating, extracting or separating a prion protein in or from a sample, such as a human or animal-derived tissue, organ, or biological fluid or an environmental sample. Methods for diagnosing or monitoring prion disease in a human or animal, or tissue, organ, or biological fluid thereof, are also provided. For example, the binding materials described herein may be useful in detecting or diagnosing pathologies such as CJD, vCJD, GSS, fatal insomnia, scrapie, BSE and CWD and other TSEs by testing a biological sample, such as whole blood, blood-derived compositions or components, cells, serum, plasma, plasma derivatives, cerebrospinal fluid, urine, tears, tonsils, brain, appendix and others. The importance of detecting prion infection in an animal or individual prior to blood, tissue, or organ donation is readily understood. The binding materials are particularly useful for the removal of prion protein from a sample or biological fluid, such as whole blood, blood components, serum, plasma, plasma derivatives, and the like. Prion removal is essential when the biological fluid is transmitted to another animal or human, such as in a blood transfusion or the administration of a blood product such as a clotting factor. The binding materials are used to remove or detect all the different forms of prion protein from the sample or can be selectively chosen to remove or detect a single form of prion protein and can therefore be used to distinguish between infectious and non-infectious prion protein in the sample.

Definitions

The terms "a," "an" and "the" as used herein are defined to mean "one or more" and include the plural unless the context is inappropriate.

The term "3F4 antibody" refers to a monoclonal antibody specific to native forms of PrPc, but not native PrPsc or PrPres. The antibody has specificity for denatured forms of hamster and human PrPc, PrPsc and PrPres.

As used herein, the terms "blood-derived compositions", "blood components" and "blood compositions" are used interchangeably and are meant to include whole blood, red blood cell concentrate, plasma, serum, platelet rich and platelet poor fractions, platelet concentrates, white blood cells, blood plasma precipitates, blood plasma fractionation precipitates and supernatants, immunoglobulin preparations including IgA, IgE, IgG and IgM, purified coagulation factor concentrates, fibrinogen concentrate, plasma fractionation intermediate, albumin preparation, or various other substances which are derived from human or animal blood. The terms also include purified blood derived proteins prepared by any of various methods common in the art including ion exchange, affinity, gel permeation, and/or hydrophobic chromatography or by differential precipitation with alcohol or polyethylene glycol.

The term "PrPc" refers to the native prion protein molecule, which is naturally and widely expressed within the body of the mammalia. Its structure is highly conserved and is not associated with a disease state.

The term "PrPsc" refers to the conformationally altered form of the PrPc molecule that is believed by those skilled in the art to be associated with diseases such as TSE/prion diseases, including vCJD, CJD, kuru, fatal insomnia, GSS, scrapie, BSE, CWD, and other TSEs, including rare TSEs of captive and experimental animals. PrPsc has the same amino acid sequence as normal, cellular PrPc, but has converted some of the α-helix to β-pleated sheet and is associated with a disease state.

The term "PrPres" refers to the proteinase resistant derivatives of the PrPsc protein of molecular weight 27-30 kDa that remain following partial digestion of PrPsc with proteinase K (PK).

The term "PrPr" refers to the prion protein expressed by recombinant technology.

The term "PrP" refers to prion protein in general.

The term "bead" refers to a solid phase particle or granule to which a reactive group or binding component may be bound. Beads having an irregular shape as well as beads having spherical, oval, rod, or even angular shapes are included within the scope of this term.

The term "resin" refers to a polymeric media.

The term "polymeric" as used herein describes a compound or molecule composed of several smaller, repeating chemical or structural units (monomers).

Samples

The term "sample" is used herein to denote any solution, suspension, extract, composition, preparation, product, component, tissue, organ, cell, or other entity that is contacted with the prion binding materials according to the methods according to certain aspects and embodiments of the present invention. Samples according to certain aspects and embodiments of the present invention include, but are not limited to, biological samples, food products, environmental samples, or water samples. Biological samples include, but are not limited to: blood derived samples; brain derived samples; bodily fluids, such as, but not limited to, blood, plasma, serum, cerebrospinal fluid, urine, saliva, milk, ductal fluid, tears, or semen; biological extracts, such as collagen extracts, gland extracts, or tissue homogenates or extracts. Biological samples are derived from humans or animals, including but not limited to bovine, ovine, porcine, equine, murine, or *Cervidae* animals. Blood-derived samples include, but are not limited to, platelet concentrates, plasma protein preparations, immunoglobulin preparations, fibrinogen preparations, factor XIII preparations, thrombin preparations, factor VIII preparations, von Willebrand factor preparations, protein C preparations, or activated protein C preparation. The samples according to certain aspects and embodiments of the present invention also include, but are not limited to, pharmaceutical compositions, therapeutic compositions, a cosmetic compositions and products, food or food products, or nutritional supplement compositions. The examples of food-product samples include, but are not limited to, gelatin, jelly, milk, dairy products, collagen, or an infant formula.

The samples, according to certain aspects and preferred embodiments, include protein solutions comprising various proteins, including, but not limited to, human or animal serum albumin. For example, the samples include, but are not limited to, therapeutic products containing human serum albumin; human or animal serum albumin preparations; or preparations containing human or animal serum albumin as a stabilizer. Samples according to certain preferred embodiments of the present invention can contain a human or an animal serum albumin at concentrations up to approximately 50% (w/v), or from approximately 1% to approximately 50%, or from approximately 5% to approximately 25%. In one aspect, the present invention, in its preferred embodiments, unexpectedly and advantageously allows one to remove, separate, or bind prion proteins from or in samples with high concentrations of proteins, particularly blood proteins, such as serum albumin.

The environmental samples include but are not limited to soil, sewage or water, such as water from a source such as a stream, river, aquifer, well, water treatment facility or recreational water.

The samples include, but are not limited to, liquid samples, solid samples, or colloidal samples. A solid sample can be extracted with an aqueous solvent, an organic solvent or a critical fluid, and the resulting supernatant can be contacted with the binding materials. Examples of solid samples include, but are not limited to, animal-derived products, particularly those that have been exposed to agents that transmit prions, e.g., bone meal derived from bovine sources, brain tissue, corneal tissue, fecal matter, bone meal, beef by-products, sheep, sheep by-products, deer and elk, deer and elk by-products, and other animals and animal derived products.

Materials

The binding materials provided herein bind to peptides or polypeptides derived from the prion protein, or the entire prion molecule and can be used in a variety of separation processes, including but not limited to, chromatography, such as, but not limited to, thin-layer, column and batch chromatography; solid support and membrane separation; reactor separation; magnetic separation; immunoseparation; and colloidal separation. In one preferred embodiment, the binding materials are contained in a column such as a chromatography column, and a sample is introduced into and allowed to pass through the column so that prion proteins in the sample bind to the binding materials and are retained on the column. The other components of the sample pass through the column and may be collected. It is to be understood that use of the binding materials described herein is not limited to batch or column chromatography. A variety of configurations, modifications and variations of the use of the binding materials for binding prion proteins are envisioned and fall within the scope of the present invention. Such variations and modifications include, but are not limited to: batch processes; continuous processes; moving bed chromatography processes; low, medium, or high pressure processes; or small, medium or large scale processes. In alternative embodiments, the binding materials are on a membrane, fiber, bead, impregnated into a non-woven mesh, coating a fiber, contained within a filter housing, and the like.

Inorganic Components

In a first embodiment, the binding materials comprise an inorganic compound or component, such as, but not limited to, aluminum or silica. Preferably, the aluminum is aluminum oxide and the silica is fumed silica. Most preferably, the inorganic compounds are $Al_2O_3$; or $SiO_2$. These binding materials can be provided in a variety of forms, including but not limited to, a bead or resin. The binding materials can be used in a variety of separation processes, and may be contained in, or fashioned into, a chromatography column, a membrane, or any suitable separation device or implement, or may be used in a batch process, or may be used in any separation process allowing contacting the material with a sample under conditions allowing formation of the prion-binding material and the prion. The binding materials containing inorganic compounds can comprise a variety of functional groups. The functional groups are hydrophilic, such as positively charged, negatively charged, uncharged or neutral, hydrophobic, amphiphilic, or combinations thereof. Specific functional groups are described in more detail below. It is to be understood that functional groups can be inherently present in an inorganic compound, or the inorganic compound can be further modified to include functional groups. The functional groups include organic and inorganic functional groups.

Polymeric Components

In a second embodiment, the binding materials comprise polymeric materials or components and preferably include a polymer matrix, also referred to as a polymer matrix backbone. Optionally, one or more functional groups are attached to the polymer matrix. In a preferred embodiment the polymeric materials are resins, preferably, chromatographic resins. The polymeric polymer matrix backbone is preferably a methacrylate backbone, such as is found in, but not limited to, a commercially available TSK™, and TOYOPEARL™ or FRACTOGEL™ resin (Tosoh Bioscience, Montgomeryville, Pa.). The s include, but are not limited to, positively charged, negatively charged, uncharged, hydrophobic functional groups or combinations thereof. Specifically preferred functional groups are described in more detail below.

The binding materials take any form, or are manufactured, shaped, fashioned formed into, or applied to any solid support including, but not limited to, a bead, membrane, cartridge, filter, dipstick, microtiter plate, test tube, solid powder, cast or extrusion molded module, mesh, magnetic particle composite, or any other solid material first coated with a substance such as polyethylene, polypropylene, poly(4-methylbutene), polystyrene, polyacrylate, polyethylene terephthalate, rayon, nylon, poly(vinyl butyrate), polyvinylidene difluoride (PVDF), silicones, polyformaldehyde, cellulose, cellulose acetate, nitrocellulose, and the like. Alternatively, substances that form gels, such as proteins (e.g., gelatins), lipopolysaccharides, silicates, agarose and polyacrylamides are used. Polymers that form several aqueous phases, such as dextrans, polyalkylene glycols or surfactants, such as phospholipids, long chain (12-24 carbon atoms) alkyl ammonium salts and the like are also suitable. The binding materials are optionally dispersed throughout these components.

The binding materials are preferably in particulate, granular or bead form. Particulate binding materials preferably have a particle, or bead, size ranging from approximately 1 μm to 500 μm, and more preferably from approximately 20 μm to 150 μm.

Functional Groups

Prion binding materials according to certain aspects and embodiments of the present invention comprise functional groups. The term "functional group" is used herein to denote chemical groups, subgroups, or substructures that impart characteristic chemical, physical, or physicochemical behaviors to a molecule or a material. Functional groups described herein include, but are not limited to, hydrophilic, such as positively, negatively or uncharged or neutral, or hydrophobic. Amphiphilic or multifunctional functional groups are also envisioned and fall within the scope of the present invention. Functional groups include organic and inorganic functional groups. Preferred functional groups contain amine, phenyl or sulfite groups. A preferred amine group is a primary, secondary, tertiary, or quaternary ammonium ion such as dimethylaminoethyl (DMAE) or trimethylaminoethyl (TMAE). Other exemplary functional groups include, but are not limited to: $—CH_2—CHOH—CH_2NH_2$; $—C_6H_5$; $—(CH_2)_3—CH_3$; $—CH_2—CH_2—N^+H(C_2H_5)_2$; $—SO_2—CH_2—CF_3$; $—CH_2—CH_2—N^+H(CH_3)_2$; $—CH_2—CH_2—N^+(CH_3)_3$; $—SO_3^{2-}$. Additionally useful functional groups include sulfonyl groups and tresyl groups.

While not wanting to be bound by the present statement, it is believed that prion proteins have three different binding regions that bind to positively charged functional groups, negatively charged functional groups, and hydrophobic functional groups, respectively. Accordingly, the use of one or several binding materials, each including one or more types of functional groups, provides for increased and/or more specific identification or removal of prion from a sample. When two or more binding materials are used, a sample is contacted with the two or more binding materials simultaneously or in succession in any order. The binding materials, therefore, are preferably composed of two or more binding materials each containing either a positively charged functional group, a negatively charged functional group, an uncharged functional group or a hydrophobic functional group. When the binding materials are particulate in form and column chromatography is used, each different type of binding material may be in the same column or in different columns. In a more preferred embodiment, three binding materials are used, one having a positively charged functional group, one having a negatively charged functional group, and one having a hydrophobic functional group.

As used herein, the term "positively charged functional group" refers to any chemical moiety that carries a net positive charge. Non-limiting examples of positively charged functional groups include amino containing groups such as primary amines, diethylaminoethyl, dimethylaminoethyl, trimethylaminoethyl and quaternary amino groups. The term "negatively charged functional group" refers herein to any chemical moiety that carries a net negative charge. The term "uncharged functional group" refers herein to any chemical moiety that is neutral or carries no charge. Non-limiting examples of negatively charged functional groups include sulfite containing groups. Furthermore, the term "hydrophobic functional group" refers to any group that resists being wetted by water, including alkyl, aromatic, siloxane and fluorinated functionalities. Non-limiting examples of hydrophobic functional groups are phenyl and butyl containing groups. The term "amphiphilic functional group" refers to a group that is both hydrophobic and hydrophilic.

In certain aspects and embodiments of the present invention, the prion binding material contains a positively charged functional group, a negatively charged functional group, an uncharged or neutral functional group, a hydrophobic functional group, an or both. An example of a negatively charged functional group is a sulfite containing group. An example of a positively charged functional group is an amino group. An example of an uncharged functional group is a phenyl or butyl group. Examples of a hydrophobic functional group are a phenyl group or a butyl group. According to certain aspects and embodiments of the present invention, the use of amino groups, including primary, secondary, tertiary, or quaternary amino groups in the binding materials are particularly advantageous for prion binding. However, the use of various groups, depending on a particular prion protein, a sample, and conditions under which a sample and a binding material are contacted, are envisioned and fall within the scope of the present invention.

A plurality of different materials are optionally employed on the binding materials, such as laminates, for example, to impart various desirable properties to the binding materials. For example, protein coatings, such as gelatin are used to avoid non-specific binding and enhance signal detection or the like.

Surface Functionalization and Spacers

In a preferred embodiment, the binding materials possess a variety of functional groups on their surface. It is to be understood that functional groups may be inherently present on the surface of a binding material, or may be added to the surface of the binding material by procedures known to one skilled in the art. The manner of linking a wide variety of groups or compounds to various surfaces is well known and is amply illustrated in the literature.

Functional groups are for the binding of prions, according to the methods described herein, for linking additional functional groups, or for any modification of any physical, chemical, or physicochemical properties of a material, such as, but not limited to, its ionic or hydrophobic properties. Functional groups that may be present on the surface of preferred binding materials include, but are not limited to, carboxylic acids, aldehydes, amino groups, cyano groups, ethylenic groups, hydroxyl groups, mercapto groups, epoxy and the like.

In a preferred embodiment, the functional groups can include spacer groups. Spacers are groups for providing a space or a distance between the surface of a material, also referred to as a matrix or a support, and a functional group. Spacers are preferably composed of carbon, nitrogen, or oxygen atoms. In one aspect, a spacer is utilized to advantageously alter the prion-binding properties of a prion-binding material. According to certain embodiments, the spacers are up to 20 atoms in length, or up to 15 atoms in length, or 5 to 10 atoms in length. Spacers are preferably composed of, but not limited to, alkyl groups, polyethylene glycol (PEG), carbohydrate groups, amino acids, peptides up to 20 amino acids in length, or peptides from 1 to 10 amino acids in length or mixtures thereof. Most preferably, the spacers contain combinations of alkyl groups and PEG.

Commercially Available Chromatography Resins

Preferably, the binding materials are one or more of the following commercially available chromatography resins: FRACTOGEL™ EMD; TOYOPEARL™ Amino, Butyl, Phenyl, or AF-Tresyl; or TSK-GEL™ Amino, Phenyl or DEAE resins. More preferably, the binding materials include, but are not limited to: FRACTOGEL™ EMD TMAE, FRACTOGEL™ EMD $SO_3^{2-}$, FRACTOGEL™ EMD DMAE, Toyopearl™ Amino, TSK-GEL™ Amino, TSK-GEL™ Phenyl, TSK-GEL™ DEAE, TOYOPEARL™ Butyl, TOYOPEARL™ Phenyl, Aluminum oxide, TOYOPEARL™ AF-Tresyl, and silica resins. In a most preferred embodiment, the binding material is TOYOPEARL™ Amino, TSK-GEL™ Amino, TSK-GEL™ Phenyl or FRACTOGEL™ EMD $SO_3^{2-}$. The use of other commercially available chromatography resins and supports, including inorganic supports, is envisioned and falls within the scope of the present invention.

In a preferred embodiment of the present invention, the binding material includes a polymethacrylate, a hydroxyl polymethacrylate, or an AMINO 650™ resin (Tosoh Biosciences), and an amino group, such as a primary, a secondary, or a tertiary amine. The binding material according to a preferred embodiment can further include a spacer of a formula $O—R—O—CH_2—CHOH—CH_2$, wherein R is 1-10 carbons in length. The binding material is optionally applied to or fashioned into a solid support, such as a bead, a membrane or a chromatography resin.

FRACTOGEL™ EMD is a porous, beaded methacrylate resin material derivatized with hydrophilic linear polymer chains ("tentacles") that carry functional ligands. All tentacles are covalently attached to hydroxyl groups of the backbone structure.

TOYOPEARL™ and TSK-GEL™ polymer matrixes are in the form of porous, beaded methacrylate resin material derivatized with hydroxylic functionalities, and have the structure:

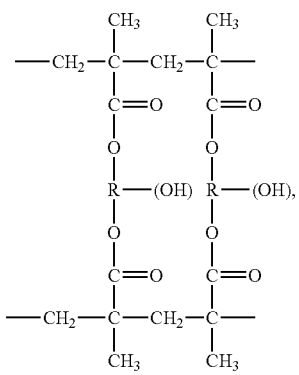

where R is a hydroxylated aliphatic group. TOYOPEARL™ AMINO 650 is a porous beaded methacrylate resin material derivatized with hydrophilic spacer chains terminating in a primary amino group, having the following chemical structure:

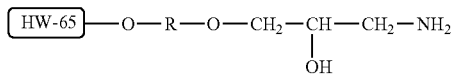

where HW-65 is the bead comprising a mean particle size of 65 μm and a mean pore size of 1000 Å, and the approximate ligand density is 100 μmol/mL.

Binding Materials Identification

In addition to the binding materials set forth above, additional binding materials can be identified as follows. Binding materials are screened for the ability to bind to prion analytes. The terms "analyte" or "analytes" as used herein refer to a multitude of molecules, including, but not limited to, a protein, a polysaccharide, and any aggregate or combination thereof. The binding materials are incubated with a sample known to contain a prion protein, unbound protein is removed, and bound protein is detected using conventional methods such as by a labeled antibody specific for prion protein. Binding materials to which the analyte has bound are identified as being suitable binding materials. Controls without primary antibody or secondary antibody are also used to eliminate non-specific binding materials.

In a preferred embodiment, the prion analyte to which the identified binding materials binds, is a prion protein found in blood or brain samples derived from a human or animal. More preferably, the analyte is found in blood or blood-derived products. It is further preferred that the analyte is associated with, or a causative factor of, a TSE in the human or animal.

Use of Binding Materials to Remove Prions

Binding materials that bind prion proteins or fragments of prion proteins are useful for a variety of analytical, preparative, and diagnostic applications. In some embodiments, the binding materials contain a solid phase, or solid surface, in the form of a bead or membrane that can be used to bind and remove prion proteins or peptides from a sample. The binding material is allowed to contact a sample, such as a biological fluid, under conditions sufficient to cause formation of a prion-binding material complex, and prion protein in the sample binds to the binding material. The binding material is then separated from the sample, thereby removing the prion protein bound to the ligand from the sample. Methods for using beads and membranes for binding protein are well known in the art such as those described in U.S. Pat. No. 5,834,318 to Baumbach et al. and PCT/US01/11150.

In some embodiments of the present invention, substantially all prion proteins are removed from a sample. By "substantially all" is meant that the concentration of prion protein is significantly reduced. In other words, transfer of all or a portion of the sample to an otherwise healthy patient carries a low risk of prion infection acceptable within public health guidelines. Substantially all prion proteins may be removed from a sample using a single binding material or multiple binding materials, simultaneously or sequentially. When using multiple binding materials, it is preferable, as described above, to use two or more binding materials, each containing a positively charged functional group, a negatively charged functional group, or a hydrophobic functional group. In a more preferred embodiment, two or more binding materials are used, each containing a negatively charged functional group or a hydrophobic functional group. A sample is contacted with the two or more binding materials in succession in any order. In a preferred embodiment, three binding materials are used wherein each contains one of a positively charged functional group, a negatively charged functional group, and a hydrophobic functional group.

In other embodiments, only particular prion materials are removed from a sample. For example, only infectious prions (PrPsc) may be removed from a sample or only non-infectious prions (PrPc) may be removed from a sample. An important discovery described herein is the identification of a multitude of binding materials having different prion specificities. Table 4 shows several binding materials and their specificities for hamster and human, non-infectious and infectious prions. Preferred binding materials for the selective removal of human PrPsc contain an amino group such as that contained in the Toyopearl™ Amino-650M or TSK-GEL™-Amino 750C chromatographic resin or functional equivalents thereof or contain a phenyl group such as that contained in TSK-GEL™ Phenyl-5PW or functional equivalents.

Preferably, the binding materials are beads packed in a column, such as a chromatography column. A sample solution, homogenate or suspension is then passed through the column either due to the force of gravity or under pressure, such as in a high pressure liquid chromatography column. Prion protein in the sample will bind to the binding materials described herein in the column. The sample passing through the column is collected and is free from prion contamination or at least has a reduced level of prion material.

Once the sample passes through the column, the bound prion protein may be eluted and collected for analysis, or if desired, for diagnostic or prognostic purposes. If it is desired to remove the prion protein from the binding material, the mobile phase of the column can be changed first to a buffer that removes poorly bound contaminants to rinse the column. The prion protein is then removed from the column by boiling or by adding a solution containing strong detergents such as Sarkosyl detergent (sodium lauryl sarcosinate, Shelton Scientific-IBI, Shelton, Conn.) or sodium dodecylsulfate (SDS), chaotropic agents, such as guanidinium hydrochloride, or agents having a low pH, such as acetic acid or by chemical modification of the binding ligand, such as for example, acetylation of an amino group.

Examples of biological samples from which prions may be removed include, but are not limited to, whole blood, blood-derived compositions or components, serum, cerebrospinal fluid, urine, saliva, milk, ductal fluid, tears, semen, or brain-derived compositions from humans or animals. Other biological samples include those that contain collagen or gland extracts. In one embodiment, prions are removed from the blood of a human or animal by using a hemodialysis circuit containing one or more binding materials described herein. In this embodiment, blood is removed from the human or animal, directed into a device containing one or more of the binding materials described herein, wherein the prion proteins are removed from the blood as they bind to the binding materials, and the prion-free or prion-reduced blood is then directed back into the human or animal.

Prion proteins may also be removed from a biological sample such as a food product (for either animal or human consumption) using the binding materials described herein. For example, the sample may contain an animal material derived or obtained from any animal, including, but not limited to, a cow, a sheep, a swine, a horse, a mouse, a hamster, or a cervidae animal. Alternatively, the sample material can be referred to as human; bovine; ovine; porcine; equine; murine, such as derived from mouse and hamster; and cervidae-derived material, such as deer and elk. Animal-derived materials from which prion proteins may be removed according to methods according to certain aspects and embodiments of the present invention include, but are not limited to, gelatin, jelly, milk, collagen, and infant formula. The sample from which prion proteins may be removed according to methods according to certain aspects and embodiments of the present invention can also include, but are not limited to, pharmaceutical compositions, therapeutic compositions, nutritional supplement compositions, food, or cosmetic compositions.

The samples, according to preferred embodiments, are protein solutions and contain various proteins, including, but not limited to, human or animal serum albumin. For example, the samples may be, but are not limited to, plasma protein preparations containing human serum albumin as a stabilizer, immunoglobulin preparations, fibrinogen preparations, factor XIII preparations, thrombin preparations, factor VIII preparations, von Willebrand factor preparations, protein C preparations, activated protein C preparations, or preparations of any combination or variation of the foregoing; therapeutic products containing human serum albumin; human or animal serum albumin preparations; and dilute protein preparations containing human or animal serum albumin as a stabilizer. The samples, according to preferred embodiments, contain a human or an animal serum albumin at concentrations up to approximately 50% (w/v), or from approximately 1% to approximately 50%, or from approximately 5% to approximately 25%. In one aspect, the present invention, in its preferred embodiments, unexpectedly and advantageously allows one to remove, separate, or bind prion proteins from or in samples with high concentrations of proteins, particularly blood proteins, such as serum albumin.

The binding materials described herein are also useful for removing prion proteins from environmental samples such as water from a source such as a stream, river, aquifer, well, water treatment facility or recreational water.

Use of Binding Materials to Detect Prions

The binding materials described herein are also useful in a method of detecting the presence of or quantifying a prion protein or peptide in a biological or environmental sample. Biological samples in which prion proteins are detected include, but are not limited to, whole blood, blood-derived compositions or components, serum, cerebrospinal fluid, urine, saliva, milk, ductal fluid, tears, semen, brain-derived compositions, feces, or the extracts or homogenates of collagens, glands, tissues (such as a tonsil or appendix), or organs. Both qualitative and quantitative methods of detection are envisioned and fall within the scope of certain aspects and embodiments of the present invention.

As described above with regard to prion protein removal, the binding materials are also useful for the detection of prion proteins in animal-derived materials used as food products. For purposes of detection, the term "animal-derived materials" refers to the materials described above as well as materials containing animal parts such as muscle, connective tissue or organ tissue. Animal-derived materials further include, but are not limited to, bone meal, beef, beef by-products, sheep, sheep by-products, elk, elk by-products, pork, pork-by products, sausage, hamburger, and baby food.

The binding materials described herein are also useful for detecting prion proteins in environmental samples such as those described above and soil extracts.

Due to the discovery of a multitude of binding materials with different prion binding characteristics, the binding materials are useful in methods for distinguishing between infectious and non-infectious prions in a single sample or between samples. Accordingly, the methods are provided for the diagnosis and prognosis of prion diseases in a human or animal. Prion diseases include, but are not limited to, transmissible spongiform encephalopathies (TSEs) such as scrapie, which affects sheep and goats; bovine spongiform encephalopathy (BSE), which affects cattle; transmissible mink encephalopathy, feline spongiform encephalopathy and chronic wasting disease (CWD) of mule deer, white-tailed deer, black-tailed deer and elk; kuru, Creutzfeldt-Jakob disease (CJD), Gerstmann-Straüssler-Scheinker Syndrome (GSS), fatal insomnia and variant Creutzfeldt-Jakob disease (vCJD), which affect humans.

In one embodiment, a sample is passed through a binding material having a higher specificity for a PrPsc than a PrPc and the bound PrPsc prion is detected using the methods described below. The same sample may then be passed through a binding material having a higher specificity for PrPc than PrPsc and the bound PrPc is detected using the methods described below. The specificities of several binding materials for PrPc and PrPsc are provided in Table 4. Preferred binding materials for the selective detection of human PrPsc contain an amino group similar to that contained in the TOYOPEARL™ TSK-GEL™-Amino 750C Amino-650M or the TSK-GEL™-Amino 750C compound or contain a phenyl group similar to that contained in TSK-GEL™ Phenyl-5PW (all resins from Tosoh Biosciences, Montgomeryville, Pa.).

When using the method provided herein to detect a prion in a sample, the sample is contacted with a binding material under conditions sufficient to cause formation of a complex between the prion protein and the binding material. The complex is then detected by conventional methods, thereby detecting the presence of the prion in the sample. For example, the binding material (a first ligand) can be labeled with a detectable label. As an alternative example, the complex is detected by labeling a secondary ligand such as an antibody or other protein, combining the labeled secondary ligand with the sample in the presence of the binding material, and detecting labeled secondary ligand-prion-binding material complex. The secondary ligand can be bound to the prion either covalently or non-covalently. A wide variety of labels and conjugation techniques are known and are reported extensively in both the scientific and patent literature. In one embodiment, the secondary ligand is labeled during its production. Suitable labels include radionucleotides, enzymes, substrates, cofactors, inhibitors, fluorescent moieties, chemiluminescent moieties, magnetic particles, and the like.

Included within the scope of certain aspects and embodiments of the present invention are methods of detecting, qualitatively and quantitatively, of a prion protein bound to a prion protein binding material, or a prion protein-prion binding material complex. The prion binding material forming a complex can be packed or fashioned into a column, a membrane, or a filter, or attached or fashioned into, or immobilized on a solid support. Also included within the scope of certain aspects and embodiments of the present invention are methods of detecting, qualitatively and quantitatively, a prion protein bound and subsequently released from a prion-binding material.

Detection may proceed by any method including immunoblotting, Western analysis, gel-mobility shift assays, tracking of radioactive or bioluminescent markers, nuclear magnetic resonance, electron paramagnetic resonance, stopped-flow spectroscopy, column chromatography, capillary electrophoresis, or other methods that track a molecule based upon an alteration in size or charge, or both. The secondary ligand-prion complex may or may not be detached from the binding material prior to detection. Other assay formats include, but are not limited to, liposome immunoassays (LIAs), which use liposomes designed to bind specific molecules (e.g., secondary ligands) and release encapsulated reagents or markers. The released chemicals are then detected according to standard techniques.

Non-radioactive labels are often attached by indirect means. Generally, a secondary ligand molecule (e.g., biotin) is covalently bound to the binding material (first ligand). The secondary ligand then binds to a tertiary ligand (e.g., streptavidin) molecule which is either inherently detectable or covalently bound to a signal system, such as a detectable enzyme, a fluorescent compound, or a chemiluminescent compound. A number of secondary and tertiary ligands can be used. Where a secondary ligand has a natural tertiary ligand, for example, biotin, thyroxine, and cortisol, it can be used in conjunction with the labeled, naturally occurring tertiary ligands. Alternatively, any haptenic or antigenic compound can be used in combination with an antibody.

The particular label or detectable group used to detect the binding materials-prion complex is not critical. The detectable group can be any material having a detectable physical or chemical property. Such detectable labels have been well-developed and, in general, any label useful in such methods can be applied to the present method. Thus, a label is any composition detectable by spectroscopic, photochemical, biochemical, immunochemical, electrical, optical or chemical means. Useful labels include fluorescent dyes (e.g., fluorescein isothiocyanate, Texas Red, rhodamine, and the like), radiolabels (e.g., $^3$H, $^{125}$I, $^{35}$S, $^{14}$C, or $^{32}$P), enzymes (e.g., LacZ (beta galactosidase), CAT (chloramphenicol acetyltransferase), horseradish peroxidase, alkaline phosphatase and others, commonly used as detectable enzymes, either in an EIA (enzyme immunoassay) or in an ELISA (enzyme linked immunosorbent assay)), and colorimetric labels such as colloidal gold or colored glass or plastic (e.g. polystyrene, polypropylene, latex, etc.) beads. The label may be coupled directly or indirectly to the desired component of the assay according to methods well known in the art. As indicated above, a wide variety of labels may be used, with the choice of label depending on the sensitivity required, ease of conjugation of the compound, stability requirements, available instrumentation, and disposal provisions.

The secondary ligands can also be conjugated directly to signal generating compounds, e.g., by conjugation with an enzyme or fluorophore. Enzymes of interest as labels will primarily be hydrolases, particularly phosphatases, esterases and glycosidases, or oxidoreductases, particularly peroxidases. Fluorescent compounds include but are not limited to, fluorescein and its derivatives, rhodamine and its derivatives, dansyl, umbelliferone, etc. Chemiluminescent compounds include luciferin, and 2,3-dihydrophthalazinediones, e.g., luminol.

Means of detecting labels are well known to those of skill in the art. Thus, for example, where the label is a radioactive label, means for detection include, but are not limited to, a scintillation counter or photographic film as in autoradiography. Where the label is a fluorescent label, it may be detected by exciting the fluorochrome with an appropriate wavelength of light and detecting the resulting fluorescence, e.g., by microscopy, visual inspection, via photographic film, by the use of electronic detectors, such as charge coupled devices (CCDs) or photomultipliers, and the like. Similarly, enzymatic labels are detected by providing appropriate substrates for the enzyme and detecting the resulting reaction product. Finally, simple colorimetric labels may be detected simply by observing the color associated with the label. Thus, in various dipstick assays, conjugated gold often appears pink, while various conjugated beads appear the color of the bead.

The binding materials of the invention can also be used to remove or detect prion proteins or peptides extracted into solution from a solid sample material. For example, a solid sample can be extracted with an aqueous solvent, an organic solvent or a critical fluid, and the resulting supernatant can be contacted with the binding materials. Examples of solid samples include, but are not limited to, animal-derived products, particularly those that have been exposed to agents that transmit prions, e.g., bone meal derived from bovine sources. Binding materials in some embodiments can be used to detect the presence of prion protein in soil. Other solid samples include, but are not limited to, brain tissue, corneal tissue, fecal matter, bone meal, beef by-products, sheep, sheep by-products, deer and elk, deer and elk by-products, and other animals and animal derived products.

Alternatively, prions and prion-binding material complexes may be treated with proteinase K (PK). PrPc is highly sensitive to PK, while PrPsc is partially digested to form PrPres. The PrPres molecule itself is highly resistant to proteolysis. Thus, PK treatment will digest PrPc, and will convert PK sensitive PrPsc to PrPres. Following removal of PK, the PrPres can be denatured and detected by antibodies such as 3F4.

In another embodiment, binding materials according to the invention may be used for the selective concentration of PrPsc over PrPc.

Use of Binding Materials to Quantify Prions

A binding material-prion complex, or alternatively, an antibody to the prion or binding material-prion complex, can be detected and quantified by any of a number of means well known to those of skill in the art. These include, but are not limited to, analytic biochemical methods such as spectrophotometry, radiography, electrophoresis, capillary electrophoresis, high performance liquid chromatography (HPLC), thin layer chromatography (TLC), hyperdiffusion chromatography, and the like, and various immunological methods, such as, but not limited to, such as fluid or gel precipitation reactions, immunodiffusion (single or double), immunoelectrophoresis, radioimmunoassays (RLAs), enzyme-linked immunosorbent assays (ELISAs), immunofluorescent assays, and the like.

Reduction of Non-Specific Binding

When using a solid support as a component of an assay for the detection of a prion protein from a sample, one of skill in the art will appreciate that it is often desirable to reduce non-specific binding to the solid support. Means of reducing such non-specific binding are well known to those of skill in the art. Typically, this involves coating the solid support with a proteinaceous composition. In particular, protein compositions, such as bovine and human serum albumin (BSA), and gelatin, are widely used.

The invention will be described in greater detail by way of specific examples. The following examples are offered for illustrative purposes, and are intended neither to limit nor define the invention in any manner.

EXAMPLE 1

Identification of Prion-binding Materials

Eighty polymer or inorganic particles were tested by using a prion binding on-beads test by a NBT/BCIP chromagen (nitroblue tetrazolium/5-bromo-4-chloro-3-indolyl-phosphate-p-toluidine salt), as described below, using normal hamster brain homogenate. The binding results are provided in Table 1 wherein "−" means no binding and "+" means positive binding. The more "+" in a particle rating, the stronger the binding observed. Twelve particles that had at least "++" were evaluated further. Table 2 summarizes the twelve particles in their ability to bind to normal hamster prion. A higher score indicates an increased amount of prion binding.

TABLE 1

Screening Polymeric Material or Inorganic Particles for Prion Protein Binding

| Reference No. | Name | Manufacturer | Binding Results |
|---|---|---|---|
| 1 | Toyopearl ™ Amino-650M | Tosoh Bioscience (Montgomeryville, PA) | +++ |
| 1' | Acetylated Amino-650M | Acetylation done by North Carolina State University (NCSU) using Toyopearl ™ Amino 650M | − |
| 2 | TSK-GEL ™ Amino 750C | Tosoh Bioscience | +++ |
| 3 | Toyopearl ™ Epoxy 700EC | Tosoh Bioscience | + |
| 4 | Toyopearl ™ AF-Carboxy-650M | Tosoh Bioscience | − |
| 5 | Toyopearl ™ AF-Heparin-650M | Tosoh Bioscience | + |
| 6 | Amberchrom ™ CG-71 m | Tosoh Bioscience | − |
| 7 | Amberchrom ™ CG-300 m | Tosoh Bioscience | − |
| 8 | Toyopearl ™ HW-40C | Tosoh Bioscience | − |
| 9 | Toyopearl ™ HW-50F | Tosoh Bioscience | − |
| 10 | Toyopearl ™ AF-Chelate-650M | Tosoh Bioscience | − |
| 11 | Toyopearl ™ DEAE-650M | Tosoh Bioscience | + |
| 12 | Toyopearl ™ DEAE-650C | Tosoh Bioscience | − |
| 13 | Toyopearl ™ Super Q-650M | Tosoh Bioscience | + |
| 14 | Toyopearl ™ Super Q-650C | Tosoh Bioscience | + |
| 15 | Toyopearl ™ QAE-550C | Tosoh Bioscience | − |
| 16 | Toyopearl ™ CM-650M | Tosoh Bioscience | − |
| 16' | Toyopearl ™ CM-650C | Tosoh Bioscience | − |
| 17 | Toyopearl ™ SP-650M | Tosoh Bioscience | − |
| 18 | Toyopearl ™ SP-550C | Tosoh Bioscience | − |
| 19 | TSK-GEL ™ Ether-5PW | Tosoh Bioscience | − |
| 20 | TSK-GEL ™ Phenyl-5PW | Tosoh Bioscience | +++ |
| 21 | Toyopearl ™ Butyl-650C | Tosoh Bioscience | ++ |
| 22 | Toyopearl ™ Phenyl-650C | Tosoh Bioscience | ++ |
| 23 | Toyopearl ™ Hexyl-650C | Tosoh Bioscience | − |
| 24 | TSK-GEL ™ DEAE-5PW | Tosoh Bioscience | +++ |
| 25 | TSK-GEL ™ Q-5PW | Tosoh Bioscience | + |
| 26 | Toyopearl ™ AF-Tresyl 650M | Tosoh Bioscience | ++ |
| 27 | Amberlite ™ XAD-7 HP | Supelco (Bellefonte, PA) | − |
| 28 | Amberlite ™ XAD-1180 | Supelco | − |
| 29 | Diaion/sepabeads ™ HP 20SS | Supelco | − |
| 30 | Diaion/sepabeads ™ SP 207 | Supelco | + |
| 31 | MCI Gel CHP 20P | Supelco | − |
| 32 | Silica gel grade 7754 | Supelco | − |
| 33 | Davisil ™ Silica gel grade 634 | Supelco | − |
| 34 | Davisil ™ Silica gel grade 643 | Supelco | − |
| 35 | Blue rayon trisulfonated (syn: Copper Phthalocyamine) | Supelco | Not tested. It is blue rayon fiber. |
| 36 | Amberlite ™ IRC-718 | Supelco | − |
| 37 | Diaion ™ CR 20 | Supelco | − |
| 38 | Amberlite ™ IRA-958 | Supelco | − |
| 39 | Dowex ™ MSA-1 | Supelco | − |
| 40 | Amberlite ™ IRA-910 | Supelco | + |
| 41 | Diaion ™ PA 418 | Supelco | − |
| 42 | Fractogel ™ EMD DMAE 650(S) | E. Merck (Gibbstown, NJ) | ++++ |
| 43 | Fractogel ™ EMID Phenyl 1 650(s) | E. Merck | − |

TABLE 1-continued

Screening Polymeric Material or Inorganic Particles for Prion Protein Binding

| Reference No. | Name | Manufacturer | Binding Results |
|---|---|---|---|
| 44 | Fractogel ™ EMD TMAE 650(S) | E. Merck | +++++ |
| 45 | Fractogel ™ EMD Propyl 650(S) | E. Merck | − |
| 46 | Fractogel ™ EMD Amino (M) | E. Merck | − |
| 47 | Fractogel ™ EMD $SO_3^{2-}$ 650(S) | E. Merck | ++ |
| 48 | Fractogel ™ EMD $COO^-$ 650(S) | E. Merck | + |
| 49 | PMMA Poly(methylmethacrylate) | Bangs Laboratories (Fishers, IN) | − |
| 50 | Aluminum oxide − 100 + 325 | Aldrich (Milwaukee, WI) | ++ |
| 51 | Polyethylene | Aldrich | − |
| 52 | Aluminum oxide − 100 + 400 | Aldrich | + |
| 53 | Poly(styrene/maleic anhydride) | Sigma Chemical Co. (St. Louis, MO) | − |
| 54 | Aminomethylpolystyrene resin | Aldrich | − |
| 55 | Aluminum oxide, activated | Aldrich | − |
| 56 | Silica, fumed | Aldrich | ++ |
| 57 | PVDF SOLVAY 1008/1001 | Solvay (Auburn Hills, MI) | ++++ (nonspecific)* |
| 58 | PVDF SOLVAY 1015/1001 | Solvay | +++ (nonspecific)* |
| 59 | Silica gel for column, 35-70 um | Acros (Pittsburgh, PA) | − |
| 60 | Silica gel 60-200 mesh | Acros | − |
| 61 | PolyStyrene, 0.93 um | Bangs | Not tested, emulsion |
| 62 | Bangs Lab Silica, 0.20 um | Bangs | Not tested, emulsion |
| 63 | Bangs Lab Silica, 0.97 um | Bangs | Not tested, emulsion |
| 64 | 1,2 DAP[1] - Epoxy 700EC | Aldrich | − |
| 65 | 1,3 DAP - Epoxy 700EC | Aldrich | − |
| 66 | 1,4 DAB[2] - Epoxy 700EC | Aldrich | − |
| 67 | L-Lysine - Epoxy 700EC | Aldrich | + |
| 68 | TETA[3] - Epoxy 700EC | Aldrich | + |
| 69 | Prometic CG-1083 | Prometic BioSciences (Cambridge, UK) | ++++ (nonspecific)* |
| 70 | Prometic CG-1085 | Prometic BioSciences | + (nonspecific)* |
| 71 | Prometic CG-1086 | Prometic BioSciences | + (nonspecific)* |
| 72 | Prometic CG-1082 (purple) | Prometic BioSciences | + (nonspecific)* |
| 73 | Prometic CG-1084 (purple) | Prometic BioSciences | ++ (nonspecific)* |
| 74 | Prometic CG-1087 (purple) | Prometic BioSciences | + (nonspecific)* |
| 75 | Prometic CG-1014 (purple) | Prometic BioSciences | ++ (nonspecific)* |
| 78 | Prometic CG-1107 (purple) | Prometic BioSciences | ++++ (nonspecific)* |
| 79 | Prometic CG-1108 (purple) | Prometic BioSciences | ++++ (nonspecific)* |
| 76 | Ethylenediamine, polymer-bound | Aldrich | − |
| 77 | Pharmacia Source 30Q | Pharmacia (Piscataway, NJ) | + |
| 80 | Clear-Base Resin (HCl) | Peptide International (Louisville, KY) | − |

[1]DAP: diaminopropane
[2]DAB: diaminobutane
[3]TETA: triethylenetetramine
[4]Amberchom ™ is a registered trademark of Rohm and Haas Company (Philadelphia, PA)
*Nonspecific: means the negative control without antibody 3F4 has the same signal as the ones tested with antibody 3F4.

TABLE 2

Ability of Polymeric Binding Materials to Bind Normal Hamster Prion (HaPrPc)

| Polymer Compounds | Base Resin | Manufacturer | HaPrPc |
|---|---|---|---|
| Fractogel ™ EMD TMAE 650(S) | PMMA** | E. Merck | 5 |
| Fractogel ™ EMD $SO_3^{2-}$ 650(S) | PMMA | E. Merck | 2 |
| Fractogel ™ EMD DMAE 650(S) | PMMA | E. Merck | 4 |
| Toyopearl ™ Amino-650M | PMMA | Tosoh Bioscience | 3 |
| TSK-GEL ™ Amino 750C | PMMA | Tosoh Bioscience | 3 |
| TSK-GEL ™ Phenyl-5PW | PMMA | Tosoh Bioscience | 3 |
| TSK-GEL ™ DEAE-5PW | PMMA | Tosoh Bioscience | 3 |
| Toyopearl ™ Butyl-650C | PMMA | Tosoh Bioscience | 2 |

TABLE 2-continued

Ability of Polymeric Binding Materials to
Bind Normal Hamster Prion (HaPrPc)

| Polymer Compounds | Base Resin | Manufacturer | HaPrPc |
|---|---|---|---|
| Toyopearl ™ Phenyl-650C | PMMA | Tosoh Bioscience | 2 |
| Aluminum oxide – 100 + 325 | $Al_2O_3$ | Aldrich | 2 |
| Aldrich silica, fumed | $SiO_2$ | Aldrich | 2 |
| Toyopearl ™ AF-Tresyl 650M | PMMA | Tosoh Bioscience | 2 |

**PMMA: Polymeric methacrylate.

The prion binding on-beads test by NBT/BCIP was performed as follows. When starting with normal PrP from a 10% hamster brain homogenate, the sample was solubilized with 0.5% Sarkosyl (200 µL of 10% to 4 ml brain) for 30 minutes at room temperature on an agitator. The sample was centrifuged at 14,000 rpm for five minutes. The supernatant was removed and a dilution of the supernatant was made in a desired media. Ninety-six well microtiter plates (Cat. No. 3075, Becton Dickinson, Franklin Lanes, N.J.) and Millipore MultiScreen-DV plates (Cat. No. MADV N65 10, Millipore Corporation, Bedford, Mass.) were first blocked with 200 µL/well of 1% (W/V) casein from Pierce (Rockford, Ill.) at 65° C. for one hour. Ten milligrams (10 mg) dry beads were swollen in 1 ml 10 mM PBS pH 7.4 and washed twice. The microtiter plates were emptied and 20-30 µL of a suspension of swollen beads was added to each well. The suspension was allowed to settle, and surplus water was removed.

Normal hamster brain homogenate was diluted 1:10 in 5% human serum albumin (Alpha Therapeutic Corp. Los Angeles, Calif.) which had already been heat-treated at 60° C. for ten hours. The suspension was added to a volume of 150 µL per well and incubated at room temperature for 1.5 hours with the beads. The unbound protein solution was removed, and 100 µL of 3F4 monoclonal antibody (Signet Laboratories, Inc., Dedham, Mass.), diluted 1:4000 in 1% casein was added to the experimental wells. Control wells contained 100 µL of 1% casein. The beads were incubated with 3F4 overnight at 4° C. with gentle agitation.

The beads were then washed twice with 10 mM PBS+10 µM $CuCl_2$ at pH 7.4. The secondary antibody, anti-mouse IgG alkaline phosphatase conjugate (#A3688, Sigma, St. Louis, Mo.), which was diluted 1:1000 in 1% casein, was added at a volume of 100 µwell/well. The samples were incubated for one hour at room temperature with shaking. All of the beads were transferred to Millipore (Bedford, Mass.) MultiScreen-DV plates to perform the washes. The samples were washed three times with PBS+$Cu^{2+}$+Tween 20 (0.05%) at pH 7.4, 3× with PBS+$Cu^{2+}$, twice with 1M NaCl and twice with 50 mM Tris.HCl+5 mM $MgCl_2$ at pH 9.5.

The 1-Step NBT/BCIP substrate was mixed well and 100 µL was added directly to each well until desired color development (light purple). Typical incubations were from five to fifteen minutes. A filter paper (#1703932, BioRad, Hercules, Calif.) was cut to shape and wetted with distilled water. Bead suspension was added into the blot wells of S&S Minifold I Dot-Blot System (Schleicher-Schuell Bioscience, Keene, N.H.) under vacuum. The wells were rinsed with water and the results scanned into a computer.

EXAMPLE 2

Identification of Prion-Binding Materials

Identification of prion-binding materials was performed using hamster brain homogenate in batch format, using two different detection systems. In the first, the amount of prion bound to a material was detected by staining the beads after incubation with the target material. The second method detected the amount of prion present in the unbound fraction contained in flow-through and wash samples using SDS-PAGE and western blots. A detailed description of each methodology is described below.

As shown in Table 3 below, the Toyopearl™ Amino-650M, TSK-GEL™ Amino 750C and TSK-GEL™ Phenyl-5PW provided the most specific binding of hamster brain PrPc.

TABLE 3

| Results of Secondary Screening | | |
|---|---|---|
| Polymer Particles | Binding evaluated by on-bead tests with NBT/BCIP | Binding evaluated by western blot with ECL-plus |
| Toyopearl ™ Amino-650M | +++ | +++ |
| TSK-GEL ™ Amino 750C | +++ | +++ |
| TSK-GEL ™ Phenyl-5PW | +++ | ++++ |
| Toyopearl ™ Butyl-650C | ++ | + |
| Toyopearl ™ Phenyl-650C | ++ | + |
| TSK-GEL ™ DEAE-5PW | +++ | 5+ (nonspecific) |
| Toyopearl ™ AF-Tresyl 650M | ++ | − |
| Fractogel ™ EMD DMAE 650(S) | ++++ | 5+ (nonspecific) |
| Fractogel ™ EMD TMAE 650(S) | +++++ | 5+ (nonspecific) |
| Fractogel ™ EMD $SO_3^{2-}$ 650(S) | ++ | +++ |
| Aluminum oxide − 100 + 325 | ++ | + |
| Aldrich silica, fumed | ++ | 5+ (nonspecific) |

For the on-bead detection method, 96-well microtiter plates (Cat. no. 3075, Falcon, Becton Dickinson, Franklin Lanes, N.J.) and Millipore Multiscreen-DV plates (Cat. no. MADV N65 10, Millipore, Bedford, Mass.) were blocked with 200 μL/well of 1% (w/v) casein at 65° C. for 1 hour. Aliquots of 10 mg of each polymer were soaked in 1 mL of 10 mM PBS pH 7.4 and washed twice. The microtiter plates were drained and 20-30 μL of a suspension of resin was added to each well. The resin was allowed to settle and the excess solution removed. To the resins was added 150 μL of a 1:10 solution of normal hamster brain homogenate in 5% human serum albumin. The mixture was incubated for 1.5 hours at room temperature. The wells were drained and 100 μL of 3F4 antibody (1:4,000) in 1% casein was added to each well and incubated overnight under refrigeration and gentle agitation. Beads were then washed twice with 10 mM PBS+10 μM $CuCl_2$, pH 7.4, followed by addition of 100 μL/well of secondary antibody alkaline phosphatase conjugate (Cat no. A3688, Sigma, St. Louis, Mo.) and incubation for 1 hour at room temperature under gentle agitation.

All the wells were drained and the beads transferred to the Multi-Screen plates, where they were washed three times with 10 mM PBS+10 μM $CuCl_2$+0.05% Tween 20 at pH 7.4, followed by 10 mM PBS+10 μM $CuCl_2$, twice with 1M NaCl, twice with 50 mM Tris-HCl+5 mM $MgCl_2$ at pH 9.5.

The washed beads were then reacted with 100 μL of NBT/BCIP substrate for 5-15 minutes for color development. Beads were transferred to filter paper using an S&S Minifold I Dot-Blot System and had the resulting color evaluated.

For the unbound fraction detection, 100 μL of each bead sample previously wetted with 10 mM PBS pH 7.4 at 4° C. overnight were placed into microfuge tubes. After washing with PBS at least four times, the beads were transferred to Ultrafree-MC 0.45 μm filter units (UFC30HVNB, Millipore, Bedford, Mass.) and rinsed again with PBS. Ten percent hamster brain homogenate (HBH) was treated with 0.5% Sarkosyl and diluted 1:10 and 1:20 in PBS. A 200 μL aliquot of it was added to each bead sample and incubated for eight minutes under agitation followed by a two-minute centrifugation at 10,000 rpm to recover the unbound fraction. Aliquots of 26-μL of flow-through were placed in 0.7 mL microcentrifuge tubes and stored at −20° C. for Western blot analysis.

The samples were thawed before Western blot, and 10 μL of sample buffer (NuPAGE LDS Sample buffer, NP0007, Invitrogen, Carlsbad, Calif.) and 4 μL of reducing agent (NuPAGE Sample Reducing Agent, NP0004, Invitrogen) (DTT, IM in $H_2O$) were added. The solution was incubated at 90-100° C. for ten minutes. The samples were applied to a 15-well NuPAGE 4-12% Bis-Tris Gel (NP0323, Invitrogen). To each well of a gel, 17 μL was applied for a western blot analysis and 14 μL for a protein stain gel. The volume of molecular weight marker (MultiMark Multi-Colored Standard, LC5725, Invitrogen) was 5 μL. Western blots used PVDF membranes, 1% casein as blocker, 1:10,000 of 3F4 as primary antibody, 1:3000 of goat anti-mouse horseradish peroxidase (HRP) conjugate as secondary antibody and ECL plus as substrate. Films were exposed for six minutes.

Samples with high PrP binding to the binding materials produce no signal in the flow-through and are scored "5+". Those having no binding are scored "−". The other samples are graded between these values.

EXAMPLE 3

Determination of Prion-binding Specificity

Generally, wetted beads composed of different binding materials were quantitatively placed into individual disposable columns. The columns contained frits small enough to retain the beads but large enough to permit flow-through of the challenge solutions. The challenge solutions were prion-containing brain homogenates in Sarkosyl (Sigma) spiked into red blood cell concentrate comixtures. More specifically, the challenge solutions contained TSE-infectious human brain homogenates, infectious hamster brain homogenates, noninfectious human brain homogenates, or noninfectious hamster brain homogenates. The challenge solutions were allowed to pass through the target binding material for a defined period of time, while the flow-through was being collected. Beads were then rinsed and quantitatively transferred from their columns into collection vials from which known quantities were removed for subsequent processing to determine specific prion binding and nonspecific protein binding. The flow-through solution and the remainder of the reacted beads were also stored for potential future analysis.

Using the methods that are described in more detail below, the binding activity of eleven binding materials for prion proteins was determined as described in Table 4. The binding materials are ranked (with a ranking of 1 being the binding material exhibiting the largest amount of binding to prion proteins) for the ability to bind either normal or infectious human or hamster prion protein. For example, the Fractogel™ EMD TMAE 650(S) binding material (having a methacrylate backbone and the functional group —$CH_2$—$CH_2$—$N^+(CH_3)_3$) bound the largest quantities of both hamster and human infectious prion protein (PrPsc), and the Fractogel™ EMD $SO_3^{2-}$ 650(S) binding material (having a methacrylate backbone and the functional group —$SO_3^{2-}$) bound the largest quantities of both hamster and human normal prion protein. These quantities were measured by releasing bound protein from the prion binding material, separating the released proteins by electrophoresis, and using Western blot to analyze immunoreactivity of protein released from the binding material with a prion-specific monoclonal antibody. The binding of the antibody to prion proteins was detected by chemiluminescence. Quantification was achieved by comparing the darkness of electrophoretic bands on film (indicated antibody bound to prion protein that had been bound to the binding material) with control bands of 2 ng, 10 ng and 50 ng of mouse IgG, and assigning a score value to the binding materials. Rankings for binding materials having the same score were established by comparing the sample bands to each other directly.

TABLE 4

Ranking of 11 polymer compounds based on their ability to bind to normal hamster prion (HaPrPc), normal human prion (HuPrPc), infectious hamster prion (HaPrPsc) and infectious human prion (HuPrPsc) after secondary screening.

| Polymer Compounds and functional group | Base Resin | Manufacturer | HaPrPc | HuPrPc | HaPrPsc | HuPrPsc |
|---|---|---|---|---|---|---|
| Fractogel ™ EMD TMAE 650(S) $—CH_2—CH_2—N^+(CH_3)_3$ | PMMA | E. Merck | 2 | 2 | 1 | 1 |
| Fractogel ™ EMD $SO_3^{2-}$ 650(S) $—SO_3^{2-}$ | PMMA | E. Merck | 1 | 1 | 10 | 9 |
| Fractogel ™ EMD DMAE 650(S) $—CH_2—CH_2—N^+H(CH_3)_2$ | PMMA | E. Merck | 3 | 3 | 2 | 7 |
| Toyopearl ™ Amino-650M $—CH_2—CHOH—CH_2NH_2$ | PMMA | Tosoh Bioscience | 6 | 10 | 4 | 4 |
| TSK-GEL ™ Amino 750C $—CH_2—CHOH—CH_2NH_2$ | PMMA | Tosoh Bioscience | 5 | 9 | 3 | 3 |
| TSK-GEL ™ Phenyl-5PW $—C_6H_5$ | PMMA | Tosoh Bioscience | 7 | 5 | 5 | 2 |
| TSK-GEL ™ DEAE-5PW $—CH_2—CH_2—N^+H(C_2H_5)_2$ | PMMA | Tosoh Bioscience | 4 | 7 | 6 | 8 |

TABLE 4-continued Ranking of 11 polymer compounds based on their ability to bind to normal hamster prion (HaPrPc), normal human prion (HuPrPc), infectious hamster prion (HaPrPsc) and infectious human prion (HuPrPsc) after secondary screening.

| Polymer Compounds and functional group | Base Resin | Manufacturer | HaPrPc | HuPrPc | HaPrPsc | HuPrPsc |
|---|---|---|---|---|---|---|
| Toyopearl ™ Butyl-650C —$(CH_2)_3$—$CH_3$ | PMMA | Tosoh Bioscience | 8 | 4 | 8 | 5 |
| Toyopearl ™ Phenyl-650C $C_6H_5$ | PMMA | Tosoh Bioscience | 9 | 6 | 9 | 6 |
| Aluminum oxide – 100 + 325 | $Al_2O_3$ | Aldrich | 10 | 8 | 7 | 10 |
| Toyopearl ™ AF-Tresyl 650M $SO_2$—$CH_2$—$CF_3$ | PMMA | Tosoh Bioscience | 11 | 11 | 11 | 11 |

Preparation of Dry Beads

Dry beads were prepared in bulk by wetting the beads with a 20% methanol solution in water. The beads were left for at least 24 hours before using. When the original amount of dry beads was between 0.5 g and 2.5 g, the pre-wetted bead slurry was transferred to a 50 ml plastic conical tube. The excess liquid was drawn off and 25 ml of 20% methanol was added. The sample was then gently shaken or tumbled for 30 seconds. When the original bead weight was outside of these aforementioned limits, the volume of methanol was adjusted using 10 ml for less than 0.5 g of resin and 40 ml for 2.5 to 4.0 g. The beads were allowed to settle by gravity for approximately 12-15 minutes or until most of the whole beads were at the bottom of the tube. The supernatant solution (including fines) was carefully drawn off and discarded. The methanol rinse was repeated once more and then 20% methanol was added to make a 1:1 (v/v) bead slurry. The beads were stored at 4° C.

Preparation of Bead Slurry

Four hundred and forty microliters (440 μl) of bead slurry was transferred into a 15 ml plastic conical tube (220 μL of wet beads per column used), and 10 ml of the working buffer (20 mM Citrate buffer/140 mM NaCl, pH 7.0) was added. The sample was gently shaken or tumbled for 30 seconds. The beads were allowed to settle by gravity for approximately 12-15 minutes or until most of the whole beads were at the bottom of the tube. The supernatant solution (including fines) was carefully drawn off and discarded. The working buffer rinse was repeated two more times, and a sufficient volume of working buffer was added to yield a 1:1 volume ratio. The sample was again gently shaken or tumbled for 30 seconds, allowed to settle and let stand overnight at room temperature. The volume of working buffer was kept at 1:1 by any necessary addition of working buffer, and the hydrated beads were held in buffer at 4° C. until use.

Preparation of Pre-Hydrated Beads

Amino Toyopearl™ and other beads were obtained as wet slurries in 20% ethanol, and did not require additional hydration steps. However, equilibration to working buffer was performed as follows. The manufacturers estimate the commercial slurries to contain approximately 72% resin by volume, and 300 μL of slurry per column was used. The beads were transferred to a 15 ml plastic tube (e.g. Falcon) and 10 ml of the working buffer was added. The sample was gently shaken or tumbled for 30 seconds. The beads were allowed to settle by gravity for approximately 12-15 minutes or until most of the whole beads were at the bottom of the tube. The supernatant solution (including fines) was carefully drawn off and discarded. The working buffer rinse was repeated two more times, and a sufficient volume of working buffer was added to yield a 1:1 volume ratio. The sample was again gently shaken or tumbled for 30 seconds, allowed to settle and let stand overnight at room temperature. The volume of working buffer was kept at 1:1 by any necessary addition of working buffer and the hydrated resin was held in buffer at 4° C. until use.

Preparation and Handling of Red Blood Cells

A bag of 110 ml Adsol™ (Baxter, Bloomington, Ind.) was added to approximately 250 ml bag of red blood cell concentrates (RBC) containing about 250-300 ml RBC and residual white blood cells and platelets. The resulting hematocrit (volume of red blood cell (RBC)/total volume) was about 50-55%. Adsol™:CPD (citrate phosphate dextrose) and RBCs were mixed by inversion. The mixture was then passed through a Pall leukoreduction filter (Pall Corporation, East Hills, N.Y.) at room temperature within eight hours from collection and placed in a new bag. This process decreased the amount of leukocytes in the RBC mixture. The leukofiltered RBC were held in the new bag at 4° C. for up to 42 days. The final composition of the buffer mixture in this preparation was 30.6% Adsol/8.5% CPD v:v. Prior to use, the percent hemolysis of the RBC preparation was checked by measuring the absorbance at 415 nm of the supernatant following centrifugation. RBC preparations that had greater than a 2% increase hemolysis over the hemolysis value obtained immediately after preparation were not used.

Preparation and Handling of Brain Homogenate

Normal hamster brain homogenate (10% w/v) was prepared by Dr. Robert Rohwer and colleagues at the University of Maryland according to their established methods. Aliquots were prepared in 1.8 ml volumes and held frozen at −80° C. or on liquid nitrogen until use. Alternatively, they were thawed once for aliquoting. Sixty microliters of brain homogenate was used per column in each experiment.

Following thawing of a brain homogenate sample, the sample was placed on wet ice. Then 6.6 μL of 5% Sarkosyl reagent (0.5 g of Sarkosyl dissolved in 9.5 ml of CPD:Adsol buffer (8.5% CPD, 30.6% Adsol and 60.9% PBS v:v:v)) was added to each 60 μL aliquot of thawed brain homogenate. The sample was vortexed and rocked gently on wet ice for 30 minutes to allow for denaturation. The sample was then centrifuged at 14,000 rpm in a microcentrifuge for five minutes at 4° C. The supernatant was transferred to a new tube, and the pellet discarded. The supernatant was held on wet ice for a maximum of one hour. The resulting supernatant was a 10% brain homogenate containing 0.5% Sarkosyl reagent. Treated aliquots were applied to the columns no later than one hour after preparation and held on wet ice during handling.

Quantitative Transfer of Hydrated Beads to Columns To each empty column, 750 µL of 0.1% Tween™ 20 solution was added. One milliliter of 20% Ethanol (v:v) was then added to each column and allowed to flow under gravity. A further 2×1 ml of degassed, deionized water was added to each column to wash off the ethanol solution and remove any air remaining trapped in the frits. Using a quantitative pipettor, 400 µL of a hydrated bead suspension was transferred to a column. The excess working buffer was allowed to flow by gravity through the transferred wet beads, and the column was then washed three times with 1 ml of working buffer before introducing the samples.

Preparation of RBC Co-Mixture (Challenge Solutions)

Using a syringe and an 18 gauge (or larger) needle, 540 µL RBC/column was placed in a polypropylene conical tube. The tube was centrifuged at 3,000 rpm for ten minutes in order to separate a layer of Adsol™ onto the top. Then 60 µL of 10% treated brain homogenate was added on top of the Adsol™ layer, thereby reducing the direct contact between the RBC preparation and highly concentrated spiked material, i.e., brain homogenate and Sarkosyl detergent. The co-mixture was mixed by inversion, kept on wet ice and used within four hours of preparation. Prior to use in the column assay, the mixture was brought to room temperature for ten minutes.

Addition of Challenge Solutions to the Columns

Once all columns were filled with hydrated beads, the challenge solutions were mixed and very carefully layered over the beads at a volume of 0.5 ml/column. Solutions were allowed to flow-through the columns by gravity. Total flow time was between approximately five and twenty minutes.

The first 0.5 ml of challenge solution flow-through was collected in a 2 ml cryovial. An additional 0.5 ml of working buffer was added to each column, and the flow-through collected in the same cryovial. The bead columns were then rinsed five times with 1 ml of working buffer during which the beads were continually resuspended by pipetting to ensure a thorough and uniform wash. The beads were then recovered from the columns as described below.

Quantitative Recovery of the Bound Beads

To each column, 0.75 ml of working buffer was added. The column was flushed using a pipette to suspend the beads and the suspension was quickly transferred to a graduated tube. The bead suspension was allowed to settle within the tube and as much of the supernatant as possible was removed without disturbing the bead layer. This supernatant was then added back to the same column and the above steps repeated twice to transfer any remaining beads from the column into the tube. The beads were then allowed to settle by gravity for ten minutes, and the volume of the bead layer within the graduated tube was recorded.

Preparation of Bound Beads for Analysis

First, the level of working buffer in each tube was adjusted to 1 ml, and a suspension of the beads was made by gently vortexing the tube. Using a pipette, 500 µL of the suspension was removed and transferred to a small Eppendorf™ (Brinkmann instruments, Westbury, N.Y.) microfuge tube. The suspension was allowed to settle for ten minutes, and the volume of settled beads was adjusted to 100 µL. The transferred beads were then centrifuged, and the supernatant removed. The bead aliquots were immediately prepared for electrophoresis and western blot analysis.

Quantitation of Dry Beads Versus Hydrated Beads

The dry weight was calculated based on volume of settled beads and swell ratio as follows:

Dry weight of beads=Settled volume/Swell ratio

Swell Ratio=Hydrated bead Volume (µL)/Dry weight (mg)

For Toyopearl™ 42.5 mg dry weight=200 µL wet beads in 20% methanol

Swell ratio (in 20% methanol)=200/42.5=4.71

EXAMPLE 4

Western Blot Analysis

The following Western blot procedures were designed to allow for the assessment of recovered or depleted infectious and non-infectious prion proteins from solutions of brain homogenates spiked into red blood cell concentrates (RBC). These procedures were applied to samples obtained from the column prion binding assay described above in Example 3, including samples of beads exposed to the challenge solutions and samples of the challenge solutions that flowed through the columns, and were collected.

Generally, samples were derived from the column binding assay of beads having target binding materials reacted with prion-containing solutions, or from flow-through from these reactions. Prepared samples were then analyzed by Western blot for the presence of prion protein. The immunodetection of prion protein was carried out by using primary mouse monoclonal antibodies specific to prion proteins. These prion immunocomplexes were then detected with an alkaline phosphatase-conjugated secondary antibody and a chemiluminescent reaction was visualized on an X-ray film.

Gel Electrophoresis Sample Preparation

The following steps were preferably performed immediately following the column assay described in Example 3.

For every column bead sample prepared, 100 µL of well-suspended beads were mixed with 100 µL Invitrogen 2× sample buffer by vortexing. Controls were also prepared by mixing the unused brain homogenate (normal human brain, sporadic CJD brain, normal hamster brain, scrapie hamster brain, etc.) from the column assay with Invitrogen 2× Sample Buffer. More specifically, 20 µL aliquot of brain homogenate was added to 40 µL of 2× sample buffer.

A control of Mouse IgG was also prepared as follows. A standard of 50 ng per lane was prepared by mixing 20 µl of 2.5 mg/ml mouse IgG with 480 µl of PBS, which equals 100 µl/ml. Add 25 of this mixture to 475 of 2× Invitrogen sample buffer to yield a 5 ng/ml solution. 10 µl of this per lane gave 50 ng/lane for the high concentration direct load gel standard. Five microliters of a 100 µg/mL Mouse IgG solution was mixed with 495 µL 2× Invitrogen reduced sample buffer. This resulted in 1 ng/µL Mouse IgG; loading 10 µL of this per lane yielded 10 ng/lane (the high concentration direct-load gel standard) (10 ng/lane). A Mouse IgG low concentration direct-load gel standard (2 ng/lane) was also prepared by diluting the medium concentration standard from the previous step by mixing 50 µL of the 1 ng/µL Mouse IgG in loading buffer with 200 µL Invitrogen 2× sample buffer (resulting in 0.2 ng/µL). Loading 10 µL of this per well yielded 2 ng/lane. Invitrogen SeeBlue Plus2 Pre-Stained Molecular Weight Standards were also prepared as directed by the manufacturer.

All samples were heated in Invitrogen buffer for ten minutes at 90° C. The samples were then centrifuged briefly and stored overnight at −20° C. The heating procedure was repeated the following morning, prior to applying the samples to the SDS-PAGE gel.

Immunoreaction Procedure

After a 12% Bis Tris NuPAGE SDS-PAGE gel was loaded with the samples described above, the gel was electrophoresed for 45 minutes at constant 200 V, and an electroblot transfer procedure was performed. The membrane to which the protein was transferred was then placed in a Fisher Square Dish and incubated for one hour on a rocking platform at room temperature in 25 ml of Western Breeze blocking agent (12.5 ml water, 5 ml Diluent A, and 7.5 ml Diluent B). The blocking solution was discarded.

The membrane was incubated in a 1:5,000 dilution of Signet 3F4 primary antibody solution in 20 ml fresh Western Breeze Primary Antibody Diluent (14 ml water, 4 ml diluent A, 2 ml diluent B). The primary antibody was previously diluted 1:1 in glycerol, and therefore, the working dilution was 1:10,000. The membrane was incubated under refrigeration on a rocking platform.

The primary antibody solution was discarded and the membrane washed three times for ten minutes each in 20 ml of Western Breeze™ Antibody Wash (1.25 ml Antibody Wash Solution (16×) in 18.75 ml water) at room temperature on a rocking platform. The membrane was then incubated in 1:10,000 AP3 (KPL, Gaithersburg, Md.) secondary antibody in 20 ml Western Breeze Primary Antibody Diluent for 60 minutes at room temperature on a rocking platform. The secondary antibody solution was discarded and the membrane was washed in Western Breeze Antibody Wash as described above. The membrane was then washed with 20 ml of 20 mM Tris-HCl, 1 mM $MgCl_2$ at pH 9.8 for ten minutes at room temperature.

Chemiluminescent Development Procedure

The membrane was transferred to a dry tray and soaked with 5 ml Western Breeze pre-mixed Chemiluminescent Substrate (CDP Star™ substrate, Applied Biosystems, Foster City, Calif.) for five minutes with gentle agitation. The membrane was blotted lightly with a paper towel and then placed in a sheet protector. The membrane was then transferred in the sheet protector to a film cassette (without an intensifying screen) held at room temperature for 30 minutes and exposed to autoradiography for five minutes at room temperature.

EXAMPLE 5

Binding of Endogenous PrPc from Human Plasma

To show the ability of the prion-binding resins to remove PrPc from endogenous, unspiked with PrPc, human plasma, the following experiments were performed.

Undiluted, fresh, pooled human plasma was used for binding of endogenous PrPc by prion binding materials. Frozen, pooled human plasma was thawed at 37° C., filtered through a 0.45 µm filter, and Sarkosyl was added to a final concentration of 0.05%. Binding of plasma to columns and detection of prions was performed as described elsewhere in the present specification.

The results of testing of binding of endogenous PrPc from human plasma are depicted in FIG. 1. Panel A depicts the results of detection by Western blot of prion protein in bead eluate in the absence of Sarkosyl (lane 1 is molecular weight marker; lane 2—Mo IgG lo; lane 3—Mo IgG med; lane 4—Mo IgG high; lane 5—normal human platelets; lanes 6-7—resin a; lanes 8-9—resin b; lanes 10-11—Amino 650-M; lanes 12-13—acetylated Amino 650. Panel B depicts the results of detection by Western blot of the unbound fraction of the samples in Panel A (lane 1—molecular weight marker; lane 2—Mo IgG low; lane 3—Mo IgG med; lane 4—Mo IgG high; lane 5—normal hamster brain (nHB); lane 6—normal human platelets; lanes 7-8—resin a; lanes 9-10—resin b; lanes 11-12—Amino 650-M; lanes 13-14—acetylated Amino 650.). Panel C shows the results of detection by Western blot of prion protein the in presence of Sarkosyl (lane 1—molecular weight marker; lane 2—Mo IgG low; lane 3—Mo IgG med; lane 4—Mo IgG high; lane 5—normal hamster brain; lane 6—human platelets; lane 7—normal human plasma+Sarkosyl, 1:10; lane 8—resin a; lane 9—resin a; lane 10—resin b; lane 11—resin b; lane 12—Amino 650-1; lane 13—Amino 650-2). Panel D shows the results of detection of unbound fractions of the samples in Panel C by Western blot of prion protein in the presence of Sarkosyl (lane 1—molecular weight marker; lane 2—Mo IgG low; lane 3—Mo IgG med; lane 4—Mo IgG high; lane 5—normal hamster brain; lane 6—human platelets; lane 7—normal human plasma+Sarkosyl; lane 8—resin a; lane 9—resin a; lane 10—resin b; lane 11—resin b; lane 12—Amino 650-1; lane 13—Amino 650-2).

In reference to FIG. 1, panel A, lanes 10 and 11, and panel C, lanes 12 and 13, the binding of PrPc to Toyopearl™ Amino 650-M resin was detected, the binding was abolished if the charge on the amino group was removed by acetylation (results shown in panel A, lanes 12 and 13).

The experimental results demonstrated the ability of the resins to bind endogenous PrPc from human plasma, thereby providing evidence that the resins are useful for removal of PrP from samples obtained from humans or animals.

EXAMPLE 6

Requirement for Spacer for Binding of PrPsc from Blood Fractions

As shown in FIG. 1, Toyopearl™ Amino 650-M resin bound endogenous PrPc from human plasma. At least a portion of this resin contained a spacer arm, or group, proprietary to Tosoh™. The importance of the spacer for PrPsc binding was investigated.

Four (4) Protein Isolation Kit for Sorbent Identification (PIKSI™) columns (0.5 ml/each were packed as follows: two columns each of an experimental sample of Toyopearl™ Amino 650 M lacking a spacer; and a commercial Toyopearl™ Amino 650 M resin with a spacer. Toyopearl™ Amino 650 C resin lacking a spacer was also tested.

Two milliliters (2 ml) of 10% scrapie brain homogenate (SBH) were treated with 0.5% Sarkosyl. The columns were challenged with Sarkosyl-treated supernatant diluted with working buffer (1:100) by adding 3 ml of SBH in 297 ml of working buffer. The columns were challenged in duplicate with 10 ml of diluted SBH in buffer by loading at the flow speed of 0.5 ml/min. The flow through solutions were collected, and aliquots of resin were removed from each column and washed with 10 ml of working buffer.

Figure 2:
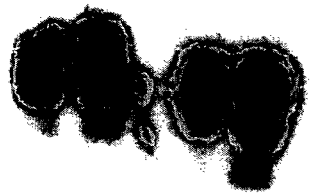
FIG. 2 is a photograph of a Western blot showing the binding of PrPsc from scrapie brain homogenate to prion binding materials and appropriate controls.

Half of each sample was subjected to proteinase K digestion with each resin and the challenge in buffer. The samples were tested Western Blots as described herein elsewhere. The results as shown in FIG. 2 (lane 1—molecular weight markers; lane 2—0.1% Sarkosyl treated SBH in buffer−PK; lane 3—0.1% Sarkosyl treated SBH in buffer+PK; lane 4—MWM; lane 5—Amino 650M (commercial)−PK (1); lane 6—Amino 650M (commercial)−PK (2); lane 7—Amino 650M (commercial)+PK (1); lane 8—Amino 650M (commercial)+PK (2); lane 9—Amino 650M (experimental)+PK (1); lane 10—Amino 650M (experimental)+PK (2); lane 11—Amino 650M (experimental)+PK (1); lane 12—Amino 650M (experimental)+PK (2); lane 13—Amino 650C−PK (1); lane 14—Amino 650C−PK (2); lane 15—Amino 650C+PK (1); lane 16—Amino 650C+PK (2)). The experimental results shown in FIG. 2 clearly indicate that the presence of a spacer arm is necessary for PrPsc binding by the Amino 650-M resin.

EXAMPLE 7

Capture of PrPc in the Presence of High Concentrations of Human Serum Albumin (HSA)

To demonstrate the ability of resins to remove PrP from a therapeutic product comprising various proteins, binding of PrPc from in the presence of human serum albumin was investigated.

Four Bio-Rad™ columns were packed with Toyopearl™ Amino 650 M amino resin. The height of the resin bed was 1 cm and the volume was 0.5 ml. The columns were rinsed abundantly with working buffer. The samples loaded on the columns were as follows:

Column I—1% nHaBH (normal hamster brain homogenate) in working buffer;

Column II—1% HaBH, 25% HSA (Sigma) in working buffer;

Column III—1% HaBH, 25% HSA (Sigma) and 20 mM N-Ac-Trp (Acros Organics, Belgium) in working buffer;

Column IV—1% HaBH, American Red Cross preparation (ARC prep).

The 20 mM N-Ac-Trp was dissolved in 25% HSA in working buffer, with shaking and heating at 37° C., for 45 minutes. The 10% nHaBH supernatant was prepared as previously described and diluted 1:10 into materials of choice (step 2) to obtain 1% nHaBH.

The bottom of each column was connected with a 4-channel peristaltic pump. Five milliliters (5 ml) of 1% nHaBH prepared in the previous step was run over columns I-IV at a flow rate of 0.5 ml/min. The columns were washed with 10 ml working buffer/column, at a flow rate of 0.5 m/min. The resins were recovered, the samples prepared as previously described and run on 12% Bis-Tris SDS-PAGE gels.

Figure 3:
FIG. 3 is a photograph of a Western blot demonstrating the capture of PrPc by prion binding materials in samples containing human serum albumin and appropriate controls.

Western blots using 3F4 primary antibody were used to detect PrPc that had been captured by the resins. The photograph of the blot is shown in FIG. 3 (lane 1—Low Mouse IgG control; lane 2—Med. Mouse IgG control; lane 3—nHaBH control; lane 4—1% HaBH column; lane 5—1% HaBH, 25% HSA column; lane 6—1% HaBH, 25% HSA, 20 mM N-AC-Trp column; lane 7—1% HaBH, ARC prep column). Bands of approximately equal intensity were seen in each lane, indicating that Toyopearl™ 650-M amino resin captured PrPc from hamster brain homogenate in the presence of 25% human serum albumin obtained from a variety of sources.

The experimental results as shown in FIG. 3 demonstrated the ability of the resins to bind a prion protein from a sample comprising HSA, thereby providing evidence that the resins are useful for binding prion proteins in variety of therapeutic products and ensuring the safety of therapeutic products in which blood proteins are used, for example, as stabilizers or therapeutic agents, and which can be contaminated with PrP.

EXAMPLE 8

Binding of PrPsc to Amino Resin in Human Serum Albumin

The binding of infectious PrPsc spiked into albumin was demonstrated in the experiment described below. 12 PIKSI columns, 0.5 ml each, were packed with Toyopearl™ Amino 650 M resin. 2 ml of 10% SBH (scrapie brain homogenate) was treated with 0.5% Sarkosyl.

The following six challenges were prepared as outlined below.

1. Challenge with SBH in buffer: dilute Sarkosyl-treated supernatant with working buffer (1:100); 0.22 ml of SBH was added to 22 ml of working buffer.
2. Challenge with SBH in HSA (American Red Cross (ARC) formulation): dilute Sarkosyl-treated supernatant with 25% HSA (1:100); 0.22 ml of SBH was added to 22 ml of HSA (American Red Cross formulation).
3. Challenge with SBH in HSA (Sigma) with N-acetyl-DL-tryptophan and Caprylate: dilute Sarkosyl-treated supernatant with 25% HSA (1:100) containing 20 mM N-acetyl Trp and 20 mM caprylate; albumin was obtained from Sigma and contained no additives; 0.22 ml of SBH was added to 22 ml of HSA solution.
4. Challenge with SBH in HSA (Sigma) with N-acetyl Trp: dilute Sarkosyl-treated supernatant with 25% HSA (1:100); 0.22 ml of SBH was added to 22 ml of HSA with 20 mM N-acetyl Trp.
5. Challenge with SBH in HSA (Sigma) with caprylate: dilute Sarkosyl-treated supernatant with 25% HSA (1:100); 0.22 ml of SBH was added to 22 ml of HSA with 20 mM caprylate.
6. Challenge with SBH in HSA (Sigma) alone: dilute Sarkosyl-treated supernatant with 25% HSA (1:100); 0.22 ml of SBH was added to 22 ml of HSA (Sigma).

Figure 4:
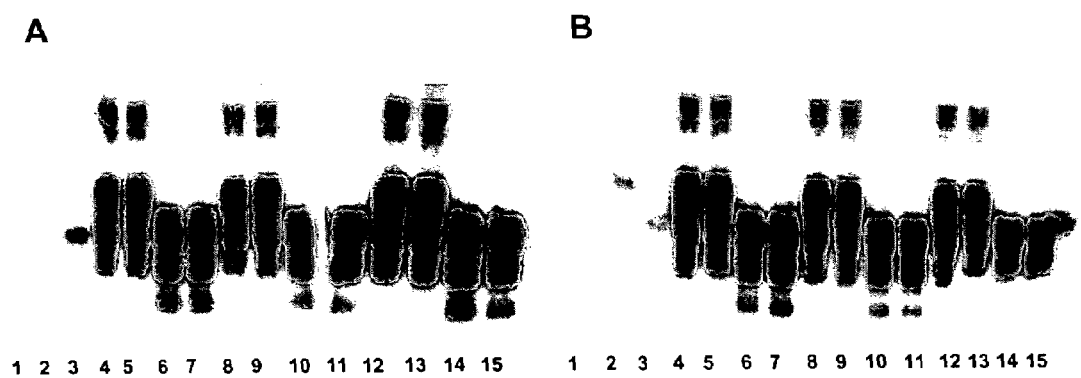
FIG. 4 is a photograph of a Western blot demonstrating removal with a resin comprising an amino functional group of PrPres spiked into human serum albumin.

Each resin was challenged in duplicate with 10 ml of solution. The columns were loaded at a flow rate 0.5 ml/min controlled with a peristaltic pump. The flow-through solutions were collected, as was the resin from each column. Proteinase K digestion was conducted with each resin and challenge in buffer. The samples were subjected to Western blots according to the method described herein. The blots are depicted in FIG. 4 (panel A: lane 1—Molecular Weight Standard; lane 2—0.1% Sarkosyl-treated SBH in buffer−PK; lane 3—0.1% Sarkosyl-treated SBH in buffer+PK; lane 4—SBH in buffer−PK(1); lane 5—SBH in buffer−PK(2); lane 6—SBH in buffer+PK(1); lane 7—SBH in buffer+PK(2); lane 8—SBH in HSA (ARC formulation)−PK(1); lane 9—SBH in HSA (ARC formulation)−PK(2); lane 10—SBH in HSA (ARC formulation)+PK(1); lane 11—SBH in HSA (ARC formulation)+PK(2); lane 12—SBH in HSA (Sigma)−PK(1); lane 13—SBH in HSA (Sigma)−PK(2); lane 14—SBH in HSA (Sigma)+PK(1); lane 15—SBH in HSA (Sigma)+PK(2); lane; Panel B: lane 1—Molecular Weight Standard; lane 2—0.1% Sarkosyl-treated SBH in buffer−PK; lane 3—0.1% Sark-treated SBH in buffer+PK; lane 4—SBH in HSA (Sigma) with AcetylTrp−PK(1); lane 5—SBH in HSA (Sigma) with AcetylTrp−PK(2); lane 6—SBH in HSA (Sigma) with AcetylTrp+PK(1); lane 7—SBH in HSA (Sigma) with AcetylTrp+PK(2); lane 8—SBH in HSA (Sigma) with Caprylate−PK(1); lane 9—SBH in HSA (Sigma) with Caprylate−PK(2); lane 10—SBH in HSA (Sigma) with Caprylate+PK(1); lane 11—SBH in HSA (Sigma) with Caprylate+PK(2); lane 12—SBH in HSA (Sigma) with AcetylTrp & Caprylate−PK(1); lane 13—SBH in HSA (Sigma) with AcetylTrp & Caprylate−PK(2); lane 14—SBH in HSA (Sigma) with AcetylTrp & Caprylate+PK (1); lane 15—SBH in HSA (Sigma) with AcetylTrp & Caprylate+PK(2)

The results shown in FIG. 4 demonstrated that infectious PrPres was able to bind to an amino resin when combined with human serum albumin, and that a variety of additives did not interfere with binding.

Although methods and materials similar or equivalent to those described herein can be used in the practice or testing of the present invention, suitable methods and material are described above. All publications, patent applications, patents and other cited references mentioned herein are incorporated by reference in their entirety. In addition, the materials, methods, and examples are illustrative only and not intended to be limiting.

The foregoing description is provided for describing various embodiments relating to the invention. Various modifications, additions and deletions may be made to the embodiments and structures without departing from the scope and spirit of the invention.

What is claimed is:

1. A method of forming a complex between a prion protein and a prion protein binding material in a sample comprising contacting the sample with the prion protein binding material under conditions allowing formation of the complex between the prion protein and the prion protein binding material, wherein the prion protein binding material comprises a polymer matrix attached to a functional group, which polymer matrix comprises polymethacrylate, methacrylate, or a combination thereof and which functional group comprises a primary amine or trimethylaminoethyl group, and wherein the binding material binds specifically and selectively to the prion protein.

2. The method of claim 1, further comprising detecting the complex prior to a separation process from the sample, after a separation process from the sample, or both.

3. The method of claim 1, wherein the polymer matrix is in the form of (i) a porous, beaded methacrylate resin material derivatized with hydrophilic linear polymer chains; or (ii) a porous, beaded methacrylate resin material derivatized with hydroxylic functionalities, having the structure:

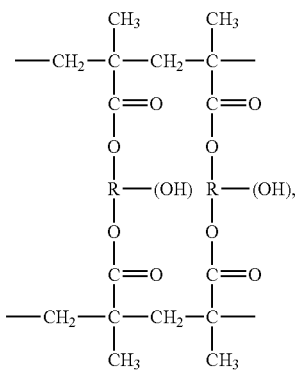

where R is a hydroxylated aliphatic group.

4. The method of claim 1, wherein the polymer matrix is a porous beaded methacrylate resin material derivatized with hydrophilic spacer chains terminating in a primary amino group, having the following chemical structure:

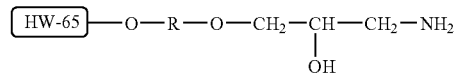

where the approximate ligand density is 100 μmol/mL and HW-65 is the methacrylate bead comprising a mean particle size of 65 μm and a mean pore size of 1000 Å.

5. The method of claim 1 wherein the prion protein is PrPc, PrPsc, PrPr or PrPres.

6. The method of claim 1, wherein the prion binding material is in a chromatography column, on a membrane, fiber or bead, impregnated into a non-woven mesh or coating of a fiber, or contained within a filter housing, or a combination thereof.

7. The method of claim 1, wherein the sample is a biological sample, a food product, an environmental sample, or a water sample.

8. The method of claim 7, wherein the biological sample is derived from a human or an animal.

9. The method of claim 8, wherein the animal is a bovine, an ovine, a porcine, an equine, a murine or a *Cervidae* animal.

10. The method of claim 1 wherein the prion protein is a human, bovine, ovine, porcine, equine, murine, or a *Cervidae* animal prion protein.

11. The method of claim 7, wherein the biological sample is a blood-derived sample; a brain derived sample; a bodily fluid sample; a collagen extract; a gland extract; or a tissue homogenate or extract.

12. The method of claim 11, wherein the bodily fluid is blood, plasma, serum, cerebrospinal fluid, urine, saliva, milk, ductal fluid, tears, or semen.

13. The method of claim 11, wherein the blood-derived sample is a platelet concentrate, a plasma protein preparation, an immunoglobulin preparation, a plasma fractionation intermediate, an albumin preparation, a fibrinogen preparation, a factor XIII preparation, a thrombin preparation, a factor VIII preparation, a von Willebrand factor preparation, a protein C preparation, or an activated protein C preparation.

14. The method of claim 1, wherein the sample is a pharmaceutical composition, a therapeutic composition, a cosmetic composition, food, or a nutritional supplement.

15. The method of claim 7, wherein the biological sample is gelatin, jelly, milk or dairy product, collagen, or infant formula.

16. The method of claim 7, wherein the biological sample comprises serum albumin.

17. The method of claim 16, wherein the serum albumin is a human serum albumin or an animal serum albumin.

18. The method of claim 16, wherein the sample comprises up to approximately 50% serum albumin by weight.

19. The method of claim 1, wherein the sample comprises from approximately 5% to approximately 25% serum albumin by weight.

20. The method of claim 1, wherein the prion protein binding material further comprises a spacer connecting the polymer matrix and the functional group.

21. The method of claim 20, wherein the spacer is 20 atoms in length or less.

22. The method of claim 20, wherein the spacer is 5 to 10 atoms in length.

23. The method of claim 1, wherein the binding material comprises two or more binding materials having the same or different functional groups and the samples are contacted with the two or more binding materials simultaneously or in succession.

24. The method of claim 2, wherein the separation process comprises chromatography, solid support separation, membrane separation, reactor separation, magnetic separation, immunoseparation; colloidal separation, or a combination thereof.

25. The method of claim 1, wherein the binding material comprises a hydroxyl group.

26. The method of claim 1, wherein the binding material comprises a primary-amine containing hydroxylated methacrylate.

* * * * *